(12) United States Patent
Brisson et al.

(10) Patent No.: US 11,540,889 B2
(45) Date of Patent: Jan. 3, 2023

(54) TENSION CONTROL IN ACTUATION OF JOINTED INSTRUMENTS

(71) Applicant: INTUITIVE SURGICAL OPERATIONS, INC., Sunnyvale, CA (US)

(72) Inventors: Gabriel F. Brisson, Albany, CA (US); Nicola Diolaiti, Menlo Park, CA (US); David W. Weir, Sunnyvale, CA (US); Dimitrios Chatzigeorgiou, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 374 days.

(21) Appl. No.: 16/762,665

(22) PCT Filed: Sep. 10, 2018

(86) PCT No.: PCT/US2018/050151
§ 371 (c)(1),
(2) Date: May 8, 2020

(87) PCT Pub. No.: WO2019/094099
PCT Pub. Date: May 16, 2019

(65) Prior Publication Data
US 2020/0275984 A1 Sep. 3, 2020

Related U.S. Application Data

(60) Provisional application No. 62/584,608, filed on Nov. 10, 2017.

(51) Int. Cl.
*A61B 34/00* (2016.01)
*A61B 34/35* (2016.01)
(Continued)

(52) U.S. Cl.
CPC .............. *A61B 34/71* (2016.02); *A61B 34/35* (2016.02); *A61B 2017/00017* (2013.01);
(Continued)

(58) Field of Classification Search
CPC .................... A61B 34/71; A61B 34/35; A61B 2017/00017; A61B 2017/00314;
(Continued)

(56) References Cited

U.S. PATENT DOCUMENTS 8,597,280 B2 12/2013 Cooper et al.
8,644,988 B2 2/2014 Prisco et al.
(Continued)

FOREIGN PATENT DOCUMENTS

CN          105690388 A      6/2016
WO     WO-2007117783 A1    10/2007
(Continued)

OTHER PUBLICATIONS

International Search Report and Written Opinion for Application No. PCT/US2018/050151, dated Apr. 12, 2020, 11 pages.
(Continued)

*Primary Examiner* — Gary Jackson
*Assistant Examiner* — Sebastian X Lukjan
(74) *Attorney, Agent, or Firm* — Fish & Richardson P.C.

(57) ABSTRACT

A medical instrument system includes actuators, a medical instrument, and a control system operably connected to the actuators. The medical instrument includes an end portion and transmission systems, each of which couples the end portion to an actuator of the actuators such that the actuators are operable to drive the transmission systems to move the end portion. The control system is configured to execute operations including determining a difference between a current configuration of the end portion and a desired configuration of the end portion, and operating the actuators
(Continued)

to apply tensions to the transmission systems based on the difference and based on constant offset tensions. The constant offset tensions are independent of current tensions experienced by the transmission systems.

26 Claims, 11 Drawing Sheets

(51) Int. Cl.
A61B 34/20 (2016.01)
A61B 34/30 (2016.01)
A61B 17/00 (2006.01)

(52) U.S. Cl.
CPC .............. A61B 2017/00314 (2013.01); A61B 2017/00398 (2013.01); A61B 2034/2061 (2016.02); A61B 2034/306 (2016.02); A61B 2034/715 (2016.02)

(58) Field of Classification Search
CPC .. A61B 2017/00398; A61B 2034/2061; A61B 2034/306; A61B 2034/715; A61B 2017/00327; A61B 2090/064; A61B 2090/066
See application file for complete search history.

(56) References Cited

U.S. PATENT DOCUMENTS

| | | | |
|---|---|---|---|
| 8,821,480 B2 | 9/2014 | Burbank | |
| 9,101,379 B2 | 8/2015 | Au et al. | |
| 2009/0292165 A1* | 11/2009 | Sugiyama | A61B 34/30 |
| | | | 600/106 |
| 2011/0003656 A1 | 1/2011 | Bennett et al. | |
| 2011/0230875 A1 | 9/2011 | Walberg et al. | |
| 2015/0088161 A1* | 3/2015 | Hata | A61B 1/009 |
| | | | 606/130 |
| 2015/0133963 A1 | 5/2015 | Barbagli | |
| 2015/0289942 A1 | 10/2015 | Au et al. | |
| 2017/0127911 A1 | 5/2017 | Yamamoto et al. | |
| 2017/0304014 A1 | 10/2017 | Au et al. | |
| 2018/0228563 A1 | 8/2018 | Smaby et al. | |

FOREIGN PATENT DOCUMENTS

| | | | |
|---|---|---|---|
| WO | WO-2011143069 A1 | 11/2011 | |
| WO | WO-2015142290 A1 | 9/2015 | |
| WO | WO-2016161449 A1 * | 10/2016 | ............. A61B 17/29 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Aflakiyan A et al., "Computed Torque Control of a Cable Suspended Parallel Robot," 3rd RSI International Conference on Robotics and Mechatronics (ICROM), Oct. 2015, pp. 749-754.

Babaghasabha R., et al., "Vision Based PID Control on a Planar Cable Robot," 22nd Iranian Conference on Electrical Engineering (ICEE), May 2014, pp. 1248-1253.

Extended European Search Report for Application No. EP18876826.1 dated Nov. 19, 2020, 13 pages.

Oh, S. and Agrawal, S., "Cable Suspended Planar Robots with Redundant Cables: Controllers with Positive Tensions," IEEE Transactions on Robotics, Jun. 2005, vol. 21(3), pp. 457-465.

* cited by examiner

TENSION CONTROL IN ACTUATION OF JOINTED INSTRUMENTS

CROSS-REFERENCE TO RELATED APPLICATIONS

This application is a U.S. National Stage Application under 35 USC § 371 and claims the benefit of International Patent Application No. PCT/US2018/050151 filed on Sep. 10, 2018, which claims priority to U.S. Provisional Patent Application No. 62/584,608, filed Nov. 10, 2017, the disclosure of each of which is hereby incorporated by reference in its entirety.

BACKGROUND

Robotic procedures often employ instruments that are controlled with the aid of a computer or through a computer interface. Such instruments may include one or more articulable portions (e.g. joints) and be controlled through the use of tension-carrying elements.

SUMMARY

In one aspect, a medical instrument system includes actuators, a medical instrument, and a control system operably connected to the actuators. The medical instrument includes an end portion and transmission systems, each of which couples the end portion to an actuator of the actuators such that the actuators are operable to drive the transmission systems to move the end portion. The control system is configured to execute operations including determining a difference between a current configuration of the end portion and a desired configuration of the end portion, and operating the actuators to apply tensions to the transmission systems based on the difference and based on constant offset tensions. The constant offset tensions are independent of current tensions experienced by the transmission systems.

In another aspect, a method of operating an instrument includes determining a difference between a current configuration and a desired configuration of an end portion of the instrument, and operating actuators to apply tensions to transmission systems. The transmission systems are coupled to move the end portion. The tensions are based on the difference and constant offset tensions. The constant offset tensions are independent of current tensions experienced by the transmission systems.

In another aspect, an instrument system includes actuators, an instrument, and a control system operably connected to the actuators. The instrument includes an end portion and transmission systems, each of which is couples the end portion to an actuator of the actuators such that the actuators are operable to drive the transmission systems to move the end portion. The control system is configured to execute operations including determining a difference between a current configuration of the end portion and a desired configuration of the end portion, and determining tensions to apply to the transmission systems based on the difference. A tension of the tensions is maintained at a maximum tension and a remainder of the tensions is no more than the maximum tension.

In another aspect, one or more non-transitory computer readable media storing instructions that are executable by a processing device is featured. Upon execution of the instructions, the processing device performs operations including determining a difference between a current configuration of an end portion of an instrument and a desired configuration of the end portion of the instrument, determining first tensions to apply to transmission systems based on the difference, and operating actuators to apply second tensions to the transmission systems. The second tensions are based on the first tensions and constant offset tensions. The constant offset tensions are independent of current tensions experienced by the transmission systems.

Advantages of the foregoing can include those described below and herein elsewhere.

In accordance with an aspect of the invention, control systems and methods for an instrument having multiple degrees of freedom use differences between a current configuration/velocity of the instrument and a desired configuration/velocity of the instrument to determine and control the forces that proximal actuators apply to the instrument through a set of transmission systems. The use of applied force and feedback indicating the resulting configuration of a medical instrument allows robotic control of the medical instrument, even if transmission systems of the instrument have non-negligible compliance between the proximal actuators and remote actuated elements. The feedback approach particularly allows precise instrument operation even when the configuration of the instrument cannot be directly inferred from the positions of the proximal actuators.

In one embodiment of the invention, the configuration of an end effector or tip is measured or otherwise determined, and the differences between the current and desired configurations of the tip are employed in determining the required joint torques and the applied forces needed to achieve the desired tip configuration. Embodiments of this control method can allow selection of the dynamic behavior of the tip, for example, to facilitate the instrument interaction with tissue, while permitting flexibility in other portions of the instrument.

In another embodiment of the invention, the configuration of each joint in an instrument is measured, and the differences between current and desired joint configurations are used to determine the actuator forces needed to move all of the joints to desired configurations.

One specific embodiment of the invention is a medical system that includes multiple joints, actuators, and transmission systems. The transmission systems have proximal ends respectively coupled to the actuators, and each of the transmission systems has a distal end attached to an associated one of the joints to allow the transmission of a force for articulation of the associated joint. A sensor in the medical system generates a measurement indicative of a configuration of the joints or the instrument tip, and a control system operates the actuators to apply forces to the transmission systems, receives the configuration measurements from the sensor, and uses the configuration measurements to determine the actuation forces applied to the transmission systems.

Although some of the examples described herein often refer to medical procedures and medical instruments, the techniques disclosed also apply to non-medical procedures and non-medical instruments. For example, the instruments, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy) or on human or animal cadavers.

DETAILED DESCRIPTION

In accordance with an aspect of the invention, a medical instrument can be controlled via transmission systems driven by actuators to reposition joints of the medical instrument and thereby move an end portion of the medical instrument. A human system operator (e.g., a surgeon) can indicate a currently desired configuration and/or a currently desired velocity for the medical instrument, while an actual configuration/velocity of the instrument can be determined or estimated, e.g., through measurements by a sensor. In some cases, the actual configuration and/or the actual velocity can be measured using a sensor that generates measurements indicative of the actual configuration and/or the actual velocity. Forces, tensions, or torques can then be selected according to the desired and measured configurations and applied through the transmission systems to move the instrument toward its desired configuration. The selection criteria for the applied force, tension, or torque can be altered if prior selections of the applied force, tension, or torque resulted in the joint overshooting or failing to reach a desired position.

Figure 1:
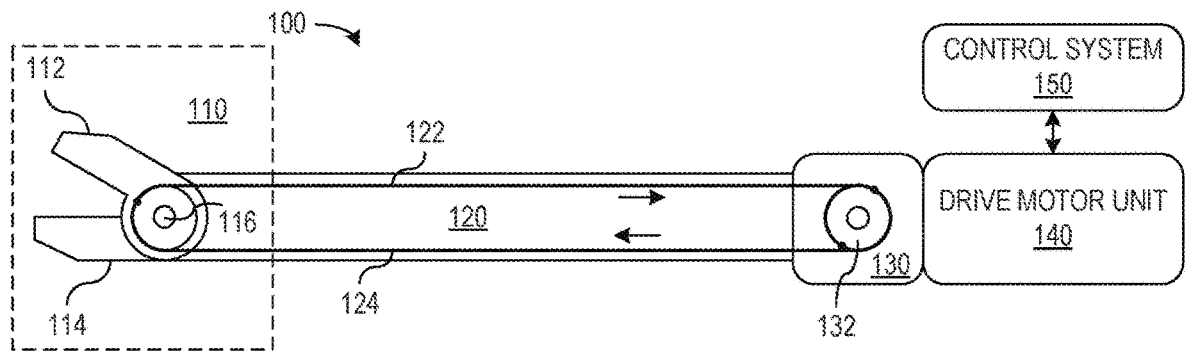
FIG. 1 illustrates features of a robotically controlled medical instrument.

FIG. 1, for example, shows a robotically controlled instrument 100 having a structure that is simplified to illustrate basic working principles of some robotically operated instruments. (As used herein, the terms "robot" or "robotically" and the like include aspects that involve teleoperation or are not teleoperated.) Instrument 100 includes a tool or end effector 110 at the distal end of an elongated shaft or main tube 120. In the illustrated example, end effector 110 is a jawed tool such as forceps or scissors having separate jaws 112 and 114, and at least jaw 112 is movable to open or close relative to jaw 114. In use during a medical procedure, end effector 110 on the distal end of main tube 120 may be inserted through a small incision in a patient and positioned at a work site within the patient. Jaws 112 may then be opened and closed, for example, during performance of surgical tasks, and accordingly must be precisely controlled to perform only the desired movements. Some implementations of instrument 100 has many degrees of freedom of movement in addition to opening and closing of jaws 112 and 114 to aid in performing procedures.

The proximal end of main tube 120 attaches to a transmission or drive mechanism 130 that is sometimes referred to as backend mechanism 130. Tendons 122 and 124 run from backend mechanism 130 through main tube 120 and attach to end effector 110. A tendon such as tendons 122, 124 may include stranded cables, rods, metal bands, tubes, or combinations of such structures, Some instruments, including medical instruments such as surgical instruments, include additional tendons (not shown in FIG. 1) that connect backend mechanism 130 to other actuated members of end effector 110, a wrist mechanism (not shown), or actuated vertebrae in main tube 120; such architecture backend mechanism 130 can manipulate the tendons to operate end effector 110 and/or other actuated elements of instrument 100.

FIG. 1 illustrates jaw 112 as having a pin joint structure 116 that provides a single degree of freedom for movement of jaw 112. Two tendons 122 and 124 are attached to jaw 112 and to a pulley 132 in backend mechanism 130, so that rotations of pulley 132 cause jaw 112 to rotate.

Pulley 132 is attached to a drive motor 140, which may be at the end of a mechanical arm (not shown), and a control system 150 electrically controls drive motor 140. In some implementations, the instrument 100 includes part or all of control system 150. In some implementations the control system 150 is partially or entirely separate from the instrument 100. In some implementations, control system 150 includes a computing system along with suitable software, firmware, and peripheral hardware. Among other functions, in some implementations control system 150 provides a user (e.g. a system operator, medical personnel or surgeon if a medical system) with an image of the work site and end effector 110 and provides a control device or manipulator that the surgeon can operate to control the movement of end effector 110. The image of the work site may be provided monoscopically, stereoscopically, etc.

The software or firmware needed for interpretation of user manipulations of the control device and for generation of the motor signals that cause the corresponding movement of jaw 112c can be complex, and are generally complex in a real robotic medical instrument. To consider one part of the control task, the generation of the control signals for drive motor 140 commonly employs the relationship between the angle or position of jaw 112 and the angle or position of drive motor 140 or pulley 132 in backend mechanism 130. If the tendons 122 and 124 are rigid (e.g., if stretching of tendons is negligible), control system 150 can use a direct relationship between the angular position of drive motor 140 and the angular position of jaw 112 as defined by the geometry of instrument 100 in determining the control signals needed to move jaw 112 as a surgeon directs. Minor stretching of tendons 122 and 124, for example, under a working load, can be handled by some mathematical models relating motor position to effector position. However, if the mechanical structure including end effector 110, tendons 122 and 124, and backend mechanism 130 has a high degree of compliance, a relationship between the angular position of motor 140 (or pulley 132) and the angular position of jaw 112 may be difficult to model with sufficient accuracy for a medical instrument.

It should be noted that in the following, the joint of the medical instrument can be a pin joint structure or a structure that provides one or more degrees of freedom of motion to the instrument tip. For instance, a joint can be a continuously flexible section or a combination of pin joints that approximates a continuously flexible section or a single rotary joint that is not purely revolute but provides also some rolling joint. See, for example, U.S. Pat. No. 7,320,700, by Cooper et Al., entitled "Flexible Wrist for Surgical Tool," and U.S. Pat. No. 6,817,974, by Cooper et Al., entitled "Surgical Tool Having a Positively Positionable Tendon-Actuated Multi-disk Wrist Joint."

It should also be noted that the actuator positions can be servo controlled to produce the desired instrument tip motion or position. Such an approach may be effective as long as the transmission systems between the actuators and the instrument joints are rigid for all practical purposes. See, for example, U.S. Pat. No. 6,424,885, entitled "Camera Referenced Control in a Minimally Invasive Surgical Apparatus." Such an approach can also be effective if the flexibility of the transmission system can be modeled exactly and a model included in the controller as described in U.S. Pat. App. Pub. No. 2009/0012533 A1, entitled "Robotic Instrument Control System" by Barbagli et Al.

Although some of the examples described herein often refer to medical procedures and medical instruments, the techniques disclosed also apply to non-medical procedures and non-medical instruments. For example, the instruments, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy) or on human or animal cadavers.

Figure 2:
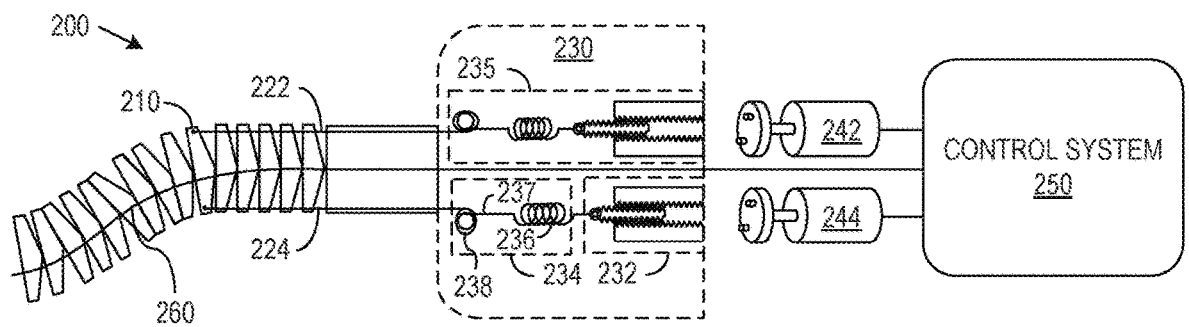
FIG. 2 illustrates a medical instrument that can be operated using a control process in accordance with an embodiment of the invention that controls the force applied through a compliant transmission system to control an articulated vertebra of the instrument.

FIG. 2 illustrates a portion of an instrument 200 that may be implemented as a compliant medical instrument. Instrument 200 has a transmission system. In addition to examples of transmission systems described herein, examples of transmission systems are further described in U.S. patent application Ser. No. 12/494,797, entitled "Compliant Surgical Device," which is hereby incorporated by reference in its entirety. Instrument 200 includes a jointed element 210 that is manipulated through control of the respective tensions in tendons 222 and 224. In general, instrument 200 may contain many mechanical joints similar to jointed element 210, and each joint may be controlled using tendons similar to tendons 222 and 224. In an exemplary embodiment, instrument 200 is an entry guide that can be manipulated to follow a natural lumen within a patient. An entry guide would typically include a flexible outer sheath (not shown) that surrounds vertebrae (including element 210) and provide one or more central lumens through which other medical instruments can be inserted for access to a work site. Compliance is particularly desirable in entry guides to prevent an action or reaction of the entry guide from harming surrounding tissue that may move or press against the entry guide. However, other types of medical instruments may also benefit from compliant drive mechanisms of the type illustrated in FIG. 2.

Instrument 200 includes a backend mechanism 230 that includes one or more transmission systems connecting an end portion, e.g., jointed element 210, to one or more actuators. For example, tendons 222 and 224 provides a compliant transmission system connecting to jointed element 210 to drive motors 242 and 244. In particular, backend mechanism 230 includes spring systems 235 attached to tendons 222 and 224 and drive motors 242 and 244. Each spring system 235 in FIG. 2 includes a mechanical drive system 232 and a constant force spring 234. Each drive system 232 couples a motor 242 or 244 and converts rotational motion of the drive motor 242 or 244 into linear motion that changes the constant force applied by the associated constant force spring 234 to tendon 222 or 224. In the illustrated embodiment, each constant force spring 234 includes a conventional Hooke's law spring 236 and a cam 238. Each spring 236 connects to an associated drive system 232 so that the linear motion of drive system 232 moves a proximal end of the spring 236. Each cam 238 has a first guide surface on which a cable 237 attached to the distal end of the associated spring 236 attaches and rides and a second guide surface on which a portion of tendon 222 or 224 attaches and rides. The guide surfaces of each cam 238 generally provide different moment arms for the action of the attached cable 237 and the attached tendon 222 or 224 and are shaped so that the tension in tendon 222 or 224 remains constant as the paying out or hauling in of a length of tendon 220 or 224 changes the force applied by the attached spring 236. Each surface of each cam 238 may be a spiral surface that extends for one or more revolutions in order to provide the desired range of movement of the tendon 222 and 224 while maintaining a constant tension in tendon 222 or 224.

Each drive system 232 controls the position of the proximal end of the corresponding spring 236 and thereby influences the amount of baseline stretch in the corresponding spring 236 and the tension in the attached tendon 222 or 224. In operation, if a drive system 232 in a spring system 235 pulls on the attached spring 236, the spring 236 begins to stretch, and if the element 210 and tendon 222 or 224 attached to the spring system 235 are held fixed, the force that spring 236 applies to cam 238 increases and therefore the tension in the attached tendon 222 or 224 increases. The tendon 222 and 224 each may include a cable or a portion of a cable. Accordingly, the tensions in tendons 222 and 224 depend linearly (in accordance with Hooke's law, the moment arms of cam 238, and the spring constant of spring 236) on movement of the proximal ends of respective springs 236, but each spring system 235 behaves asymmetrically. For example, each spring system 235 acts with constant force in response to external or distal forces that move tendon 222 or 224. Constant force spring 234 and drive system 232 can be alternatively implemented in a variety of ways such as those described further in above-referenced U.S. patent application Ser. No. 12/494,797.

Jointed element 210 has a single degree of freedom of motion (e.g., rotation about an axis) and generally moves when drive motor 242 or 244 rotates a drive system 232 to change the force applied by the attached constant force spring 234. Control system 250 can use a sensor 260 to measure the orientation of element 210. A control process as described further below uses such measurements for calculation of applied forces needed to manipulate jointed element 210 or applied torques drive motor 242 or 244 to manipulate jointed element 210.

In some cases, the drive mechanism can be compliant so that external forces can move element 210 without a corresponding rotation of drive system 232. As a result, the relationship between the position or orientation of jointed element 210 and the position of drive system 232 or drive motor 242 may not be fixed. Sensor 260 may be, for example, a shape sensor, which can sense the shape of jointed element 210 along a length of instrument 200 including element 210. Some examples of shape sensors are described in U.S. Pat. App. Pub. No. US 2007/0156019 A1 (filed Jul. 20, 2006), entitled "Robotic Surgery System Including Position Sensors Using Fiber Bragg Gratings" by Larkin et al., and U.S. patent application Ser. No. 12/164,829 (filed Jun. 30, 2008) entitled "Fiber optic shape sensor" by Giuseppe M. Prisco, the entireties of both of which are incorporated herein by reference. In some implementations, any sensor capable of measuring an angular position of jointed element 210 could alternatively be used. For example, in some cases, the sensor can correspond to a sensor associated with a drive mechanism of instrument 200, e.g., drive system 232, drive motor 242, or drive motor 244. The sensor can include an encoder, a tachometer, or other appropriate sensor to measure a position or velocity of the mechanism. Based on a kinematic relationship between position and velocity of jointed element 210 and position and velocity of the drive mechanism, the measured position or the measured velocity can be used to determine the position and the velocity of the jointed element 210.

Instrument 200 has "back driving" capability when backend mechanism 230 is detached from a motor pack, spring systems 235 still keep tendons 222 and 224 from slacking and allow the distal portion of instrument to be manually arranged (or posed) without damaging backend mechanism 230 or creating slack in tendon 222 or 224. This "back driving" capability is generally a desirable property of a surgical instrument, particularly an instrument with a flexible main tube that may be bent or manipulated during instrument insertion while the instrument is not under active control by control system 250. For example, instrument 200 can be manually posed, and the tendons within the main shaft do not experience undue tension or slack.

Figure 3A:
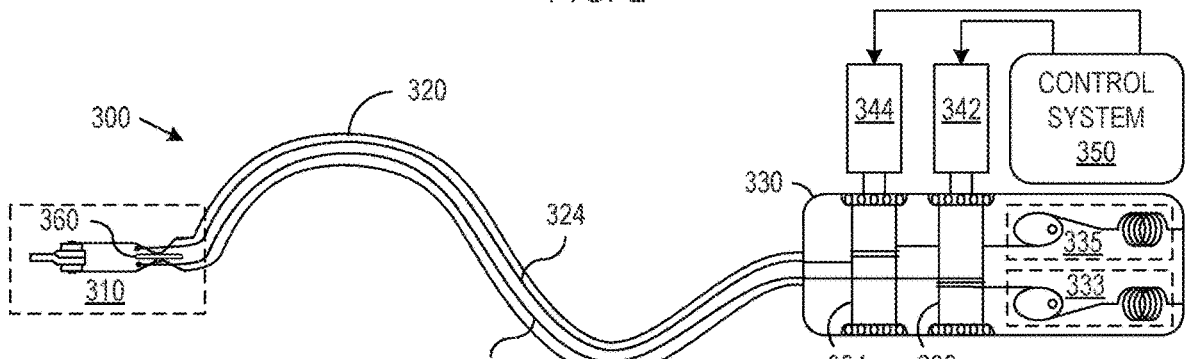
FIG. 3A illustrates a medical instrument in which a control process in accordance with an embodiment of the invention can operate with a transmission system having minimum and maximum force transfer to operate a mechanical joint.

Another example of a compliant transmission system for a joint in a medical instrument is illustrated in FIG. 3A. FIG. 3A shows an exemplary embodiment of a medical instrument 300 that uses an actuation process that permits a drive motor to freewheel or a drive tendon to slip relative to the drive motor during instrument operation as described in U.S. patent application Ser. No. 12/286,644, entitled "Passive Preload and Capstan Drive for Surgical Instruments," which is hereby incorporated by reference in its entirety. An end portion of medical instrument 300 can be manipulated. For example, the end portion can correspond to one of an end effector, a tip, or other device that can be controlled by the actuation process of medical instrument 300. In the example shown in FIG. 3A, medical instrument 300 has an end effector 310 at the end of a main tube 320, and a backend mechanism 330 manipulates tendons 322 and 324, which run through main tube 320, to control a degree of freedom of motion of end effector 310. In the illustrated embodiment, tendons 322 and 324 attach to a mechanical member in end effector 310 such that tensions in tendons 322 and 324 tend to cause end effector 310 to rotate in opposite directions about a pivot joint structure.

Figure 3B:
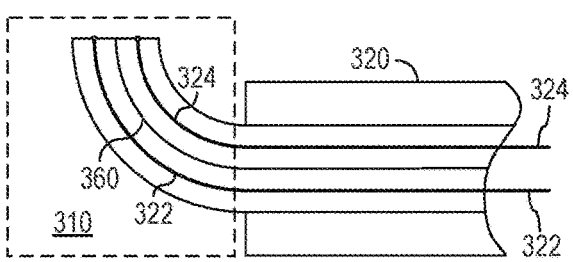
FIG. 3B shows an embodiment of the invention in which a joint includes a continuously flexible structure.

The joint structure of an end portion of instrument 300 in FIG. 3A is only an example, and other joint mechanisms for end portions of instruments that provide a single degree of freedom of motion in response to tensions applied to a pair of tendons could be employed in alternative embodiments of the invention. FIG. 3B, for example, illustrates an embodiment in which the end effector 310 includes a joint such as commonly found in catheters, endoscopes for the gastrointestinal tract, the colon, and the bronchia; guide wires; or other endoscopic instruments such as graspers and needles used for tissue sampling.

Figure 3C:
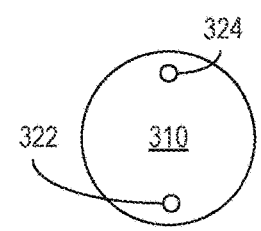
FIG. 3C illustrates positions of a pair of tendons used to control a single degree of freedom of motion in the joint of FIG. 3B.

Main tube 320 can include a catheter that is able to flex or bend in response to forces applied through tendons 322 and 324. The catheter joint may simply include an extrusion of a plastic material that bends in response to a differential in the tension in tendons 322 and 324. In one configuration, tendons 322 and 324 extend through lumens within the catheter and attach to the end of the catheter as shown in FIG. 3C. Accordingly, the forces in tendons 322 and 324 can be used to bend the catheter in the direction corresponding to the tendon 322 or 324 having greater tension. Bending of the catheter may be used, for example, to steer the catheter during insertion. In some examples, distal sensor 360 can measure the bend angle of the distal portion of the catheter to measure or compute the "joint" angle and velocity. In one particular embodiment, the bend angle can be defined as a tip orientation of the catheter with respect to the base of the distal flexible portion of the catheter. The backend and control architecture for the catheter joint of end effector 310 of FIG. 3B can be identical to that of the embodiment of FIG. 3A, except that the measured joint angle and velocity can be converted to tendon position and velocity by multiplication of the distance between the actuator cable lumen and the center of the distal flexible portion.

Backend mechanism 330, which attaches to the proximal end of main tube 320, acts as a transmission that converts torques applied by drive motors 342 and 344 into tensions in respective tendons 322 and 324 and forces or torques applied to an actuated joint in end effector 310. In the illustrated embodiment, drive motors 342 and 344 can be direct drive electrical motors that directly couple to capstan 332 and 334 around which respective tendons 322 and 324 wrap. In particular, tendon 322 wraps for a set wrapping angle (that could be less than a full turn or as large as one or more turns) around the corresponding capstan 332 and has an end that is not affixed to capstan 332 but extends from the capstan 332 to a passive preload system 333. Similarly, tendon 324 wraps for a set wrapping angle around the corresponding capstan 334 and has an end extending from the capstan 334 to a passive preload system 335. Since tendons 322 and 324 are not required to be permanently attached to capstans 332 and 334, tendon 322 and 324 may be able to slip relative to capstans 332 and 334 and relative to the shaft of drive motors 342 and 344 that respectively couple to capstans 332 and 334.

The proximal end of tendons 322 and 324 attach to respective passive preload systems 333 and 335, each of which is implemented in FIG. 3A as a cam and a spring that together act as a constant force spring. The spring can be one that generally can be modeled with Hooke's law. Passive preload systems 333 and 335 are biased, so that capstans 332 and 334 apply non-zero forces or tensions to tendons 322 and 324 throughout the range of motion of instrument 300. With this configuration, when capstans 332 and 334 are free to rotate, passive preload systems 333 and 335 control the tensions in tendons 322 and 324 and avoid slack in tendons 322 and 324 by pulling in or letting out the required lengths of tendons 322 and 324. When backend mechanism 330 is detached from motors 342 and 344, passive preload systems 333 and 335 still keep tendons 322 and 324 from slacking and allow end effector 310 and main tube 320 (when flexible) to be manually arranged (or posed) without damaging backend mechanism 330 or creating slack in tendon 322 or 324. Accordingly, instrument 300 also has "back driving" capability similar to that described above for instrument 200 of FIG. 2.

End effector 310 can be operated using drive motors 342 and 344 under the active control of control system 350 and human input (e.g., master control input in a master-slave servo control system). For example, when motor 342 pulls on tendon 322, the motor torque is transferred as an applied tension in the distal portion of tendon 322. (A maximum tension that capstan 332 can apply to proximal portion of tendon 322 depends on a tension at which tendon 322 begins to slip relative to capstan 332, but in general, the maximum tension actually used can be selected to prevent tendons 322 and 324 from slipping on capstans 332 and 334.) At the same time, when turning off the power to motor 344, allowing motor 344 and capstan 334 to freewheel, tendon 324 can be kept at its minimum tension that is the constant force that passive preload system 335 applies to proximal end of tendon 324 through the capstan 334. The larger tension in tendon 322 then tends to cause end effector 310 to rotate counterclockwise in FIG. 3A. Similarly, turning off power to motor 342 and powering motor 344 to apply force through tendon 324 to end effector 310 tends to cause end effector 310 to rotate clockwise in FIG. 3A. The ability of motor 342 and 344 to freewheel while tendons 322 and 324 are under tension and the acceptance of slippage of tendons 322 and 324 on capstans 332 and 334 do not permit control system 350 to rely on a fixed relationship between the angular positions of motor 340 and end effector 310. However, control system 350 can use a sensor 360 to measure the angular position of end effector 310 relative to the joint actuated through tendons 322 and 324.

The instruments of FIGS. 2, 3A, and 3B may have transmission systems between actuators and actuated joints provide compliance that is desirable, particularly for instruments with a flexible main tube. Transmission systems with compliance may also occur in more traditional instruments. For example, the known instrument of FIG. 1 may use sheathed or Bowden cables in sections of the instrument that bend and rod elements in straight sections. The rod elements can reduce stretching that interferes with the direct relationship of actuator and joint positions. It may be desirable in some applications to use tendons of more flexible material (e.g., polymer tendons where electrical insulation or minimal friction is desired). Such tendons may introduce an unacceptable amount of stretch for control processes relying on a direct relationship between actuator and joint position. Solid steel pull wires can also be used in or as transmission systems.

Figure 4:
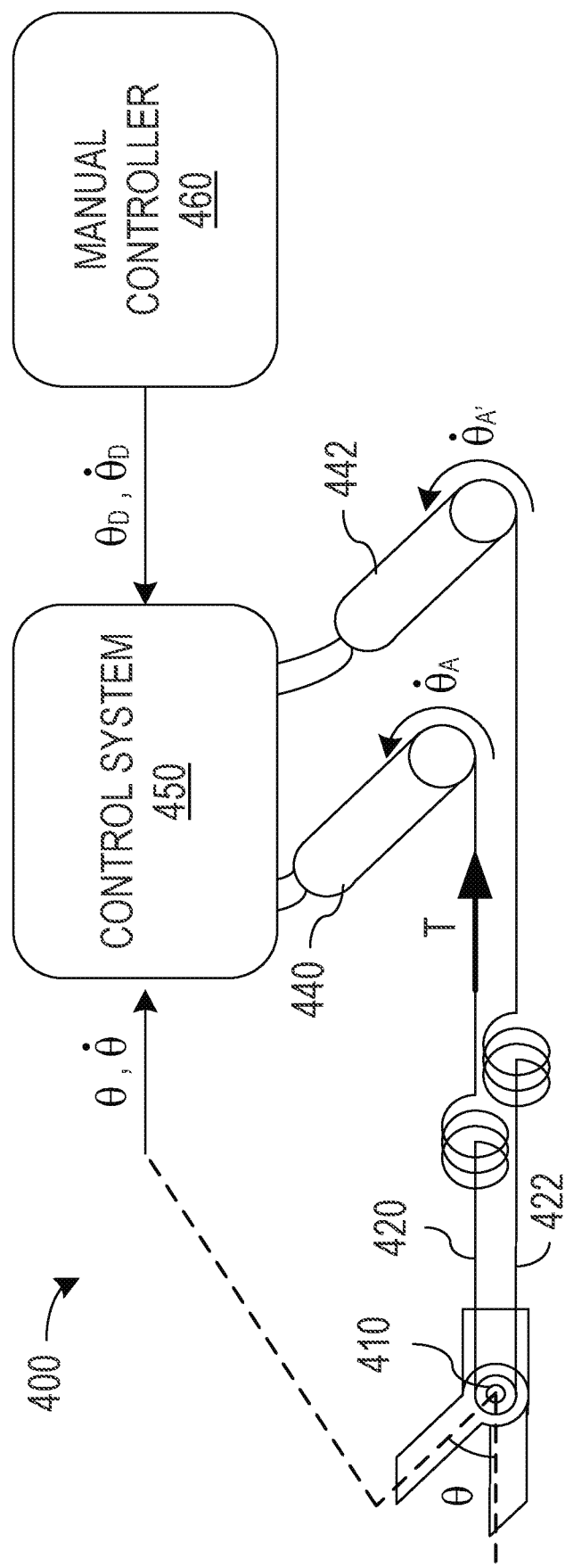
FIG. 4 schematically illustrates a robotic medical system and particularly shows quantities used in an embodiment of the invention that controls a remote joint connected to actuators through compliant transmission systems.

In accordance with one aspect of the current invention, control processes for the medical instruments of FIGS. 2, 3A, and 3B or instruments that otherwise have compliant transmission systems can employ remote measurements of the position of a mechanical joint to determine a tension to be applied to drive the mechanical joint. In another aspect, processes for the medical instruments of FIGS. 2, 3A, and 3B or instruments that otherwise have compliant transmission systems can employ measurements of the position of actuators of the instruments to determine a tension to be applied to drive the mechanical joint. The control processes could also be employed for instruments having rigid transmission systems. The control processes could also be employed for instruments having rigid transmission systems. FIG. 4 schematically shows a generalization of a medical instrument 400 having a mechanical joint 410 having a degree of freedom of motion corresponding to an angle or position θ. The term position is used broadly herein to include the Cartesian position, angular position, or other indication of the configuration of a degree of freedom of a mechanical system.

Joint 410 is connected through a transmission system 420 to an actuator 440, so that joint 410 is remote from actuator 440, e.g., joint 410 may be at a distal end of instrument 400 while actuator 440 is at the proximal end of instrument 400. In this regard, joint 410 forms part of an end portion of instrument 400. In the illustrated embodiment, transmission system 420 connects joint 410 so that a tension T applied by actuator 440 to transmission system 420 tends to rotate joint 410 in a clockwise direction. In general, transmission system 420 includes the entire mechanism used to transfer force from actuator 440 to joint 410, and actuator 440 may apply a force or torque to transmission system 420 which results in a tension in a cable or other component of transmission system 420. Such a tension can be generally proportional to the applied force or torque, so the term tension is intended to be used here without loss of generality to also indicate force or torque.

The transmission system 420 may be (but is not required to be) so compliant that a direct relationship between the position of joint 410 and the position of actuator 440 would not be accurate enough for control of joint 410. In this regard, in some examples, transmission system 420 may be compliant, but a direct relationship is sufficiently accurate for use in control of joint 410. In some cases, transmission system 420 may stretch, so that between a minimum and a maximum of tension T applied to transmission system 420, the difference in the effective length of transmission system 420 may correspond to 45° of joint articulation. In contrast, a typical medical device allows for stretching that corresponds to no more than a few degrees of joint articulation in order to be able to accurately model the position of the joint based on actuator position. It should be understood that in the general case compliance is not limited to a simple Hooke's law stretching of a spring structure. Transmission system 420 may include, for example, tendon 222 and at least a portion of backend mechanism 230 in the embodiment of FIG. 2 or tendon 322 and at least a portion of backend mechanism 330 in the embodiment of FIG. 3A. In general, the response of transmission system 420 to a tension T applied at a proximal end of transmission system 420 and to external forces applied to joint 410 or along the length of transmission system 420 may be difficult to model.

A sensor (not shown) measures position $\theta$ at remote joint 410 and provides measured position $\theta$ to a control system 450. The sensor may additionally measure a velocity $\dot{\theta}$ for the movement of joint 410, or velocity $\dot{\theta}$ may be determined from two or more measurements of position $\theta$ and the time between the measurements. The sensor can include a distal sensor in which measured position $\theta$ is provided to control system 450 through a signal wire (not shown) extending from the sensor at the distal end of instrument 400, through the main tube (not shown) of instrument 400 to control system 450 at the proximal end of the instrument. The signal wire can be an electrical wire, an optical fiber, or other signal wire capable of transmitting a signal.

Alternatively or additionally, the position of actuator 440 may be sufficiently accurate for controlling joint 410. The sensor can include a sensor associated with actuator 440, e.g., an encoder, a tachometer, or other sensor to measure a position or a velocity of actuator 440.

Actuator 440, which can include drive motor 242 or 342 of FIG. 2 or 3A, applies tension T to the proximal end of transmission system 420 and through transmission system 420 applies force or torque to joint 410. In some cases, other forces and torques can also be applied to joint 410. For example, one or more other transmission systems 420 may be connected to joint 410 and collectively apply a net tension or force that tends to cause joint 410 to rotate. In the illustrated embodiment of FIG. 4, a transmission system 422 is connected to joint 410 and to an actuator 442, so that tension in transmission system 422 tends to oppose applied tension T and rotate joint 410 counterclockwise in FIG. 4. The additional transmission system 422 or transmission systems connected to joint 410 may be the same as transmission system 420, other than a difference in where transmission system 422 or transmission systems connect to joint 410.

Control system 450 can be a general purpose computer executing a program or a circuit wired to generate a drive signal that controls a tension T that actuator 440 applies to transmission system 420. When actuator 440 is an electrical motor, the drive signal may be a drive voltage or current that controls the torque output from actuator 440, and tension T is equal to the motor torque divided by the effective moment arm at which tension T is applied to transmission system 420. As described further below, control system 450 can calculate the magnitude of tension T or the motor torque using a desired position $\theta_D$, a desired velocity $\dot{\theta}_D$ for joint 410. This calculation can be further based on one or more measurements of position $\theta$ for joint 410 at the current and prior times or one or more measurements of position $\theta_A$ of actuator 440. In this regard the position $\theta$ for joint 410 can correspond to a position that is determined based on direct measurements of the position $\theta$ for joint 410 or based on the one or more measurements of position $\theta_A$ of actuator 440. A user (e.g., a surgeon controlling a system including an instrument such as instrument 400) can provide desired position $\theta_D$ and velocity $\dot{\theta}_D$ by manipulating a controller 460. The exact configuration of controller 460 is not critical to the present invention except that controller 460 is able to provide signals from which values for the desired position $\theta_D$ and velocity $\dot{\theta}_D$ can be determined. Manual controllers suitable for complex medical instruments generally provide signals that indicate many simultaneous instructions for movements of the medical instrument, and such movements may involve multiple joints in the instrument. Suitable manipulators for use as controller 460 are provided, for example, in the master controller of the da Vinci Surgical System available from Intuitive Surgical, Inc.

The tension T needed to move joint 410 from its current position $\theta$ to desired position $\dot{\theta}_D$ in a time interval $\Delta t$ will generally depend on many factors including the effective inertia of joint 410 that resists applied tension T; the inertia of actuator 440 which applies tension T, any other transmission systems 422 coupled to joint 410 and applying a net effective force; external forces applied to joint 410; internal and external frictional forces that oppose actuation of joint 410 or movement of transmission system; the current velocity $\dot{\theta}$ of joint 410; and internal and external damping forces. Many of these factors may vary depending on the working environment of instrument 400 and may be difficult to measure or model. However, models can be developed based on system mechanics or empirically for a particular joint in a medical instrument. In one specific embodiment, control system 450 determines the tension T from the distal joint errors $(\theta_D-\theta)$ and $(\dot{\theta}_D-\dot{\theta})$, which are respectively the difference between the determined and desired positions of joint 410 and the difference between determined and desired velocities of joint 410.

Figure 5A:
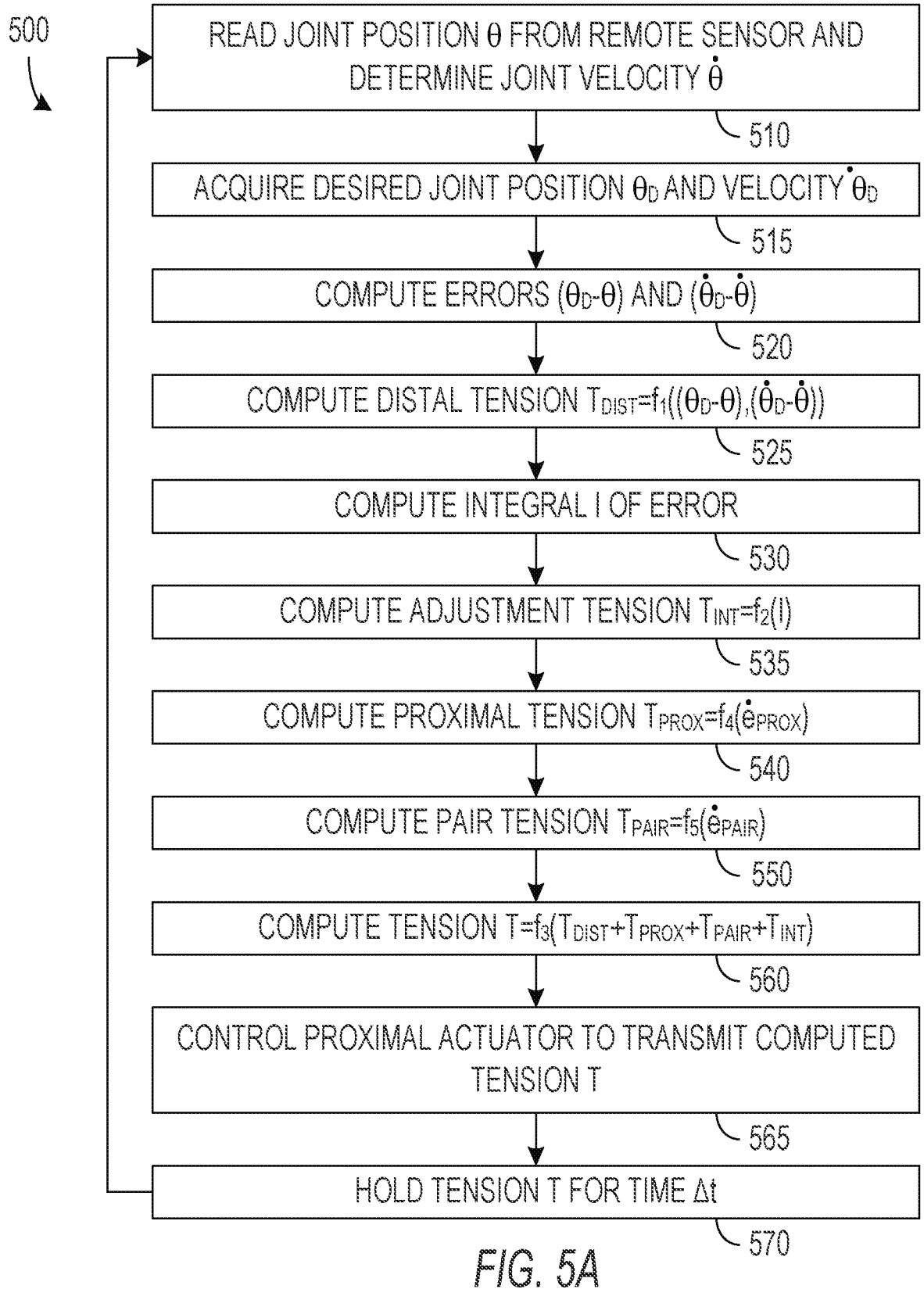
FIG. 5A is a flow diagram of a control process in accordance with an embodiment of the invention.

FIG. 5A is a flow diagram of a process 500 for controlling a medical instrument having the basic structure of instrument 400 of FIG. 4. Process 500 begins in step 510 by determining a current value of position $\theta$ of joint 410 and determining a current value for the joint velocity $\dot{\theta}$. For example, the current value of position $\theta$ of joint 410 and the current value of the joint velocity $\dot{\theta}$ can be determined from measurements taken by a sensor. Velocity $\dot{\theta}$ can be directly measured or determined or approximated using the current position $\theta$, a prior position $\theta'$, a time interval $\Delta t$ between measurements, for example, under the assumption of constant velocity (e.g., $\dot{\theta}=(\theta-\theta')/\Delta t$) or under the assumption of constant acceleration given a prior determination of velocity. For example, in some implementations, rather than directly measuring the current value of position $\theta$ for joint 410, the current value of position $\theta$ is determined based on measurements of position $\theta_A$ of actuator 440. In this regard at step 510, measurements of position $\theta_A$ of actuator 440 are taken every time interval $\Delta t$, and the current value of position $\theta$ is then determined based on the measured position $\theta_A$ of actuator 440. Similarly, a current value of velocity $\dot{\theta}$ can be determined using measurements of position $\theta_A$ of actuator 440. Alternatively, the current value of velocity $\dot{\theta}$ can be determined using measurements of a velocity $\dot{\theta}_A$ of actuator 440.

Following step 510, step 515 then acquires a desired position $\dot{\theta}_D$ and a desired velocity $\dot{\theta}_D$ for joint 410, and step 520 computes a difference or error $(\theta_D-\theta)$ between the measured and desired positions and a difference or error $(\dot{\theta}_D-\dot{\theta})$ between the measured and desired velocities.

The position error computed in step 520 can be indicative of a difference between a current configuration of an end portion, e.g., joint 410, and a desired configuration of the end portion, e.g., joint 410. The position error and velocity error can be used to determine tension T required for joint 410 to reach the desired position $\theta_D$. Tensions described herein are not necessarily applied to transmission systems. Tensions described herein can refer to tensions that are applied to transmission systems 420 or tensions that are determined or detected and used for selecting another tension to apply to transmission systems 420. In the embodiment of FIG. 5A, applied tension T may include multiple contributions, and the primary contribution is a distal tension $T_{DIST}$, which is determined as a function $f_1$ of position error $(\theta_D-\theta)$ and velocity error $(\dot{\theta}_D-\dot{\theta})$. Distal tension $T_{DIST}$ can be independent of the position of the actuator, e.g., of the angle of the motor shaft, which allows determination of distal tension $T_{DIST}$ even when there is no direct relationship between the position of joint 410 and the position of actuator 440.

In one particular embodiment, the function $f_1$ is of the form Equation 1 below, where g1 and g2 are gain factors, C is a constant or geometry dependent parameter, and $T_{sign}$ is a sign, i.e., ±1. Sign $T_{sign}$ is associated with movement of joint 410 produced by tension in transmission system 420 and may, for example, be positive (e.g., +1) if tension Tin transmission system 420 tends to increase the position coordinate $\theta$ and negative (e.g., −1) if tension T in transmission system 420 tends to decrease the position coordinate $\theta$. In another embodiment, function $f_1$ imposes a lower bound on the force, for instance, in order for the force to be always positive and sufficient to avoid slack in the transmission system. The parameter C can be a constant selected according to known or modeled forces applied to joint 410 by other portions of the system. For example, parameter C may be a constant selected to balance the torque caused by other transmission systems applying force to joint 410 or may account for expected friction or external forces. However, parameter C is not required to strictly be a constant but could include non-constant terms that compensate for properties such as gravity or mechanism stiffness that can be effectively modeled, and accordingly, parameter C may depend on the determined joint position or velocity. The gain factors g1 and g2 can be selected according to the desired stiffness and dampening of joint 410. In particular, when joint 410 is used as a static grip, the net gripping force or torque applied to tissue depends on the term $g1(\theta_D-\theta)$ of Equation 1. For example, in some implementations, the force or torque that the gripper achieves depends on this term $g1(\theta_D-\theta)$ and the commanded position. Some implementations further impose limits on the maximum torque or force that can be achieved. In general, gain factors g1 and g2 and constant C can be selected according to the desired stiffness and dampening or responsiveness of joint 410 or according to an accumulation of error. For example, when inserting the instrument 400 to follow a natural lumen within a patient, the gain factor g1 can be set to a low value to make joint 410 behave gently and prevent joint 410 from harming surrounding tissue. After the insertion, the gain factor g1 can be set to a higher value that allows the surgeon to perform precise surgical task with the instrument.

$$f_1 = T_{sign} * (g1(\theta_D-\theta) + g2(\dot{\theta}_D-\dot{\theta}) + C) \quad \text{Equation 1}$$

The term $g1(\theta_D-\theta)+g2(\dot{\theta}_D-\dot{\theta})+C$ of Equation 1 can be used to approximately determine the torque, tension, or force currently required at joint 410 to rotate joint 410 to reach the desired position $\theta_D$ using transmission system 420 in a given time $\Delta t$. In some implementations, the applied torque, tension, or force does not move joint 410 to desired position $\theta_D$ within given time $\Delta t$ but, rather, joint 410 asymptotically approaches desired position $\theta_D$ without reaching desired position $\theta_D$. The torque and force or tension are related in that the torque is the product of the force and an effective moment arm R, which is defined by the perpendicular distance between the connection of transmission system 420 to joint 410 and the rotation axis of joint 410. The effective moment arm R can either be absorbed into gain factors g1 and g2 and constant C or used to convert a calculated distal tension $T_{DIST}$ into a calculated torque.

Distal tension $T_{DIST}$, with the proper choice of function $f_1$, e.g., proper selection of parameters g1, g2, and C in Equation 1, can approximate the force that actuator 440 is required to apply to move joint 410 in a manner that is responsive to manipulations by a human operator of manual controller 460. However, optional corrections are provided by steps 530, 535, 540, and 550 under some conditions. In particular, optional steps 530 and 535 respectively compute a saturated sum or integral I of the position error $(\theta_D-\theta)$ and calculate an integral tension $T_{INT}$. The integral tension $T_{INT}$, which may be positive, zero, or negative, can be added as a correction to distal tension $T_{DIST}$, which was calculated in step 525. Integral tension $T_{INT}$ is calculated as a function $f_2$ of saturated integral I and may simply be the product of integral I and a gain factor. The saturated integral I calculated in step 530 can simply be the sum for the past N intervals of position errors $(\theta_D-\theta)$ or differences $(\theta_{D,i}-\theta_{i-1})$ between the measured position at the end of the interval and the desired position that was to be achieved. The number N of intervals involved in the sum may be limited or not, and integral I may be saturated in that the magnitude of the integral is not permitted to exceed a maximum saturation value. The saturation value would generally be selected to cap the maximum or minimum value of integral tension $T_{INT}$. However, the minimum and maximum values of integral tension $T_{INT}$ can alternatively be capped when calculating the value of function $f_2$.

Figure 5B:
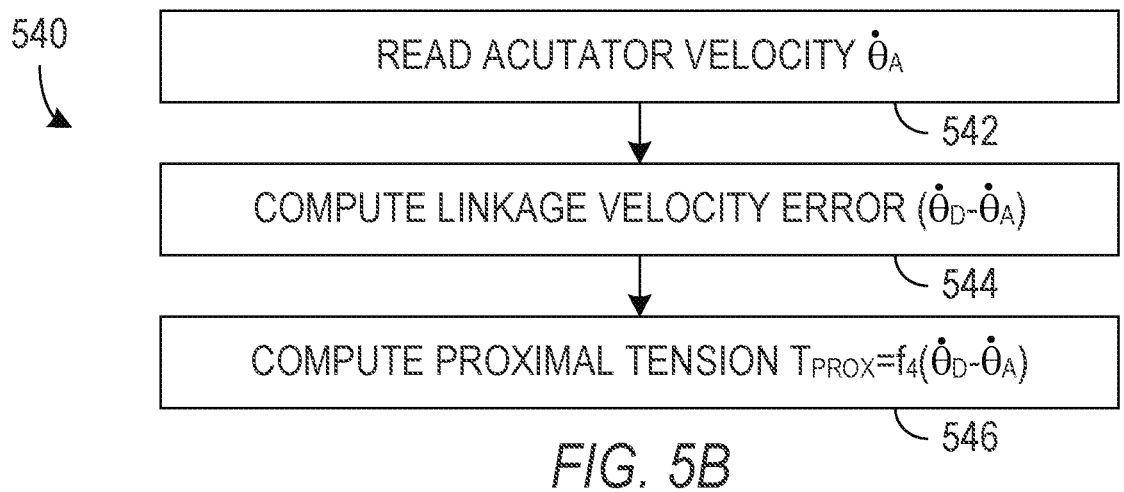
FIG. 5B is a flow diagram of a process for determining a tension correction associated with a difference between an actuator velocity and a joint velocity.

Optional step 540 computes another correction referred to herein as proximal tension $T_{PROX}$, which may be positive, zero, or negative. Proximal tension $T_{PROX}$ can be added to distal tension $T_{DIST}$, which was calculated in step 525. FIG. 5B is a flow diagram of an example process for implementing step 540 for computing proximal tension $T_{PROX}$. This example process for implementing step 540 begins in step 542 by reading a current value of a velocity $\dot{\theta}_A$ of actuator 440. Velocity $\dot{\theta}_A$ can be measured by a standard tachometer, an encoder, or other appropriate sensor that attaches at the base of actuator 440. To improve computational efficiency, step 542 can also be scheduled to run between steps 510 and 515 of FIG. 5A. Step 544 then computes the proximal velocity difference or error $\dot{e}_{PROX}$, which is defined as the difference or error between a desired velocity computed based on desired velocity $\dot{\theta}_D$ of joint 410 and the current velocity computed based on the current actuator velocity $\dot{\theta}_A$. In one particular embodiment, the desired velocity can be the product of the effective moment arm R, sign $T_{sign}$, and desired velocity $\dot{\theta}_D$ of joint 410, while the current velocity can be the product of an effective moment arm of the actuator 440 and actuator velocity $\dot{\theta}_A$. In the embodiment of FIG. 5B, proximal tension $T_{PROX}$ is determined as a function $f_4$ of proximal velocity error $\dot{e}_{PROX}$. In one particular embodiment, the function $f_4$ may simply be the product of proximal velocity error $\dot{e}_{PROX}$ and a gain factor. The gain factor can be selected to provide an additional dampening effect to transmission system 420.

Figure 5C:
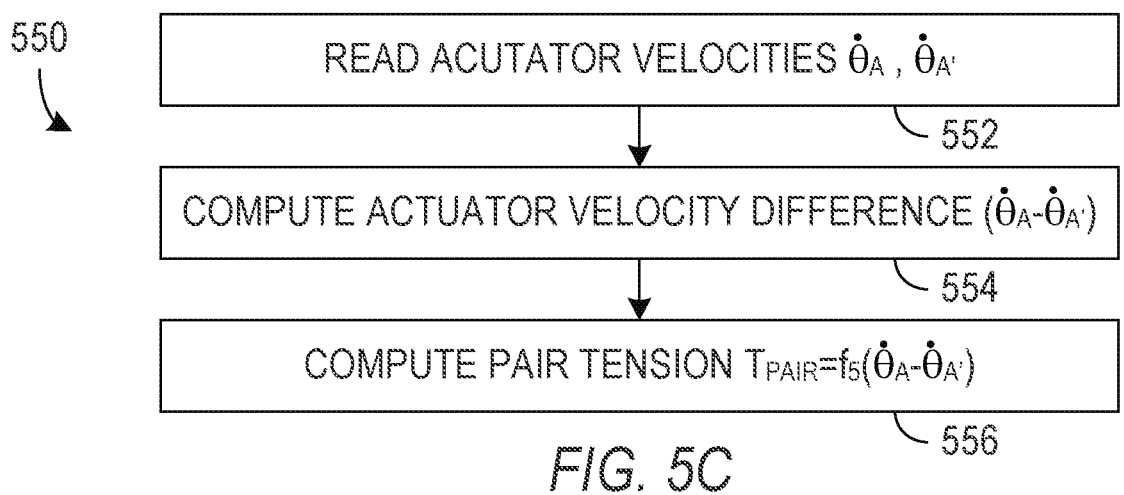
FIG. 5C is a flow diagram of a process for determining a tension correction associated with a difference between the velocities of actuators manipulating the same joint.
Figure 6:
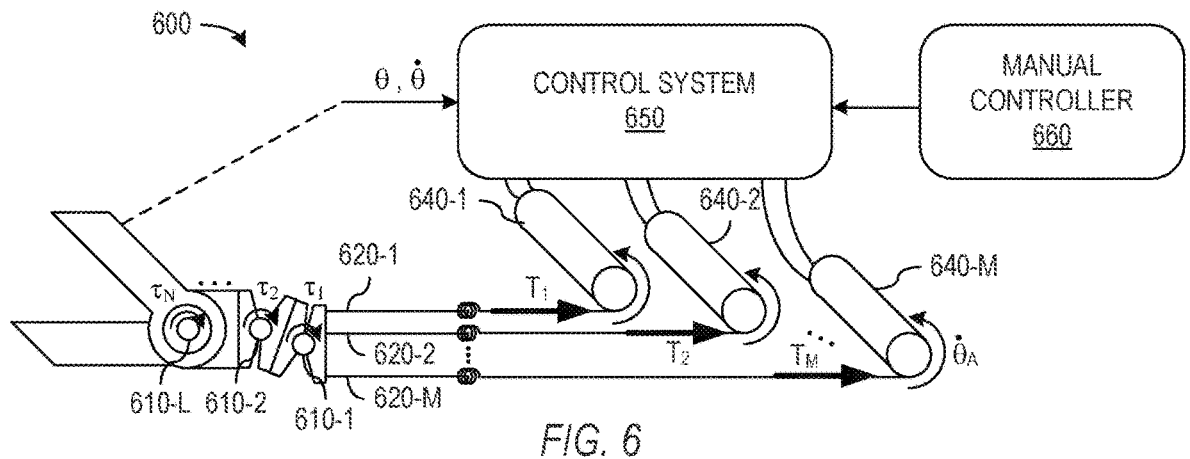
FIG. 6 schematically illustrates a robotic medical system and particularly shows quantities used in an embodiment of the invention that controls a multi jointed instrument.

Optional step 550 of FIG. 5A computes a pair tension $T_{PAIR}$, which may be positive, zero, or negative correction to distal tension $T_{DIST}$, which was calculated in step 525. FIG. 5C is a flow diagram of an example process for implementing step 550 for computing the pair tension $T_{PAIR}$. This example process 550 for implementing step 550 begins in step 552 by reading a current value of velocity $\dot{\theta}_A$ of actuator 440 and velocity values of all other actuators associated with joint 410. In the system of FIG. 4, there are two actuators 440 and 442 coupled to joint 410 and two actuator velocities $\dot{\theta}_A$ and $\dot{\theta}_{A'}$. Step 552 can be scheduled to run between steps 510 and 515 of FIG. 5A to improve computational efficiency. Step 556 then computes a pair velocity difference or error $\dot{e}_{PAIR}$, which can be defined as the difference or error between the current velocities $\dot{\theta}_A$ and $\dot{\theta}_{A'}$ of the actuators 440 and 442 associated to joint 410, when actuators 440 and 442 are substantially identical, e.g., have the same effective moment arms for operation on respective transmission systems 420 and 422. In one particular embodiment, the current velocity error $\dot{e}_{PAIR}$ can be the product of the difference $(\dot{\theta}_A - \dot{\theta}_{A'})$ and the effective moment arm of actuators 440 and 442. In the embodiment of FIG. 6, pair tension $T_{PAIR}$ is determined as a function $f_5$ of pair velocity error $\dot{e}_{PAIR}$. In one particular embodiment, the function $f_5$ may simply be the product of pair velocity error $\dot{e}_{PAIR}$ and a gain factor. The gain factor can be selected to provide additional dampening effect to transmission system 420.

Tension T is determined in step 560 of FIG. 5A as a function $f_3$ of sum of distal tension $T_{DIST}$, proximal tension $T_{PROX}$, pair tension $T_{PAIR}$, and integral tension $T_{INT}$. In some cases, constraints on maximum and minimum vales of tension T can be enforced. For example, in the embodiment of FIG. 5D, function $f_3$ limits the maximum and minimum values of tension T. Maximum tension $T_{MAX}$ and minimum tension $T_{MIN}$ can be set in the programming of control system 450 (e.g., in software). Actuators 440, 442 are operably connected to control system 450 and accordingly can be controlled by control system 450 such that tension T does not exceed maximum tension $T_{MAX}$ and such that tension T does not fall below minimum tension $T_{MIN}$. Maximum tension $T_{MAX}$ can be set to avoid damage to the instrument resulting from large forces, and minimum tension $T_{MIN}$ can be set to inhibit slack in tendons in transmission systems 420 and 422. This can ensure that tendons in transmission systems 420 and 422 do not become derailed or tangled. In some cases, only one of maximum tension $T_{MAX}$ and minimum tension $T_{MIN}$ is enforced by control system 450, while in other cases, both are enforced.

Control system 450 can initiate enforcement of maximum tension $T_{MAX}$, minimum tension $T_{MIN}$, or both maximum tension $T_{MAX}$ and minimum tension $T_{MIN}$ when instrument 400 is coupled to actuators 440, 442. In particular, maximum tension $T_{MAX}$ and minimum tension $T_{MIN}$ can be enforced upon actuators 440, 442 being coupled to transmission systems 420, 422. Instrument 400 can be configured such that tendons of transmission systems 420, 422 are slack absent any external forces on transmission systems 420, 422. In this regard, when tendons of transmission systems 420, 422 are decoupled from actuators 440, 442, the tendons can be slack. When transmission systems 420, 422 are coupled to actuators 440, 442, tension in the transmission systems 420, 422 below minimum tension $T_{MIN}$ can be detected, thereby causing control system 450 to enforce minimum tension $T_{MIN}$ and operate actuators 440, 442 in manner that causes tension T to be equal to or greater than minimum tension $T_{MIN}$. Tension T can be applied to enforce minimum tension $T_{MIN}$ and achieve desired position $\theta_D$ and/or desired velocity $\dot{\theta}_D$.

Rather than being set in software, in some cases, a compliant transmission system may itself have a minimum or maximum tension with proper design in the backend mechanism. For example, a transmission system illustrated in FIG. 3A has a minimum tension $T_{MIN}$ controlled by the setting of preload system 333 or 335 when motor/actuator 342 or 344 is freewheeling and a maximum tension $T_{MAX}$ resulting from slipping when the torque of the couple motor 342 or 344 exceeds the point when the tendon 322 or 324 slips on capstan 332 or 334.

Step 565 of FIG. 5A generates a control signal that causes actuator 440 to apply tension T calculated in step 560. For example, the control signal when actuator 440 is a direct drive electrical motor may be a drive current that is controlled to be proportional to calculated tension T. Control system 450 in step 570 causes actuator 440 to apply and hold the calculated tension T for a time interval Δt, during which time, joint 410 moves toward the current desired position $\theta_D$. When changing the tension T, the application of the full tension T will be delayed by a time depending on the inertia of actuator 440. Preferably, the inertia of actuator 440 is relatively small for rapid response. For example, the inertia of a drive motor acting as actuator 440 would preferably be less than five times the inertia of joint 410. After time Δt, process 500 branches back to step 510 to repeat measurement of the joint position, acquisition of the target position and velocity, and calculation of the tension T to be applied during the next time interval. In general, time Δt should be small enough to provide motion that appears to be smooth to the operator of the instrument and which does not cause undesirable vibrations in the instrument. For example, calculating and setting tension T two hundred and fifty times per second or more will provide movement that appears smooth to the human eye and will provide instrument operation that is responsive to human commands, e.g., to human manipulation of controller 460. Use of the errors in the calculation of the tension T will generally cause joint 410 to converge on the desired positions with or without the computation of integral tension $T_{INT}$ and without detailed modeling or measurement of the instrument or the external environment. However, as described above, parameters such as gains g1 and g2 used in calculating the applied tension T can be tuned for specific instruments and further tuned in use to compensate for changes in the external environment of the instrument.

Figure 5D:
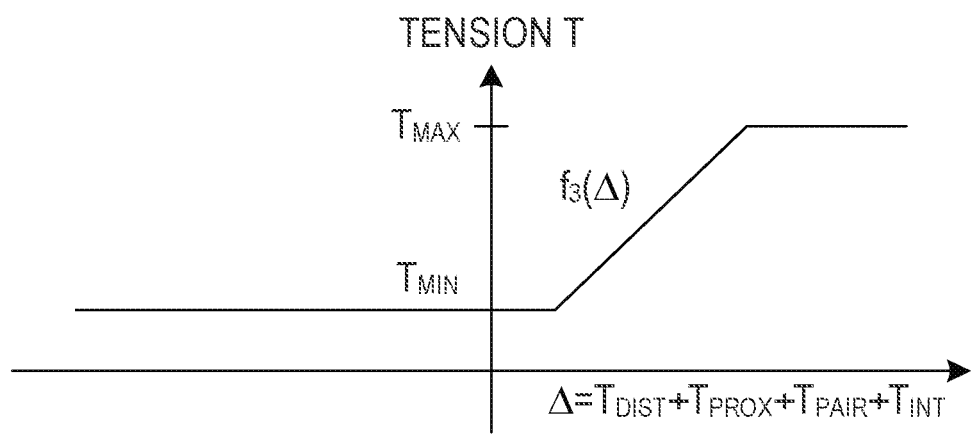
FIG. 5D illustrates a function for control of a maximum and minimum applied tension.

The tension that actuator 442 applies to transmission system 422 can also be controlled using control process 500 of FIG. 5A, and parameters used in process 500 for actuator 442 and transmission system 422 can be the same or different from those used for actuator 440 and transmission system 420 based on the similarities and differences of actuator 442 and transmission system 422 when compared to actuator 440 and transmission system 420. In particular, the sign value $T_{sign}$ for actuator 442 in the configuration of FIG. 4 will be opposite to the sign value $T_{sign}$ for actuator 440 because transmission systems 422 and 420 connect to rotate joint 410 in opposite directions. As a result, the primary tension contribution $T_{DIST}$ calculated in step 525 will typically be negative for one actuator 440 or 442. Step 560, which calculates the applied tension T, can set a negative tension sum $T_{DIST}+T_{PROX}+T_{PAIR}+T_{INT}$ to the minimum tension $T_{MIN}$ as shown in FIG. 5D. Accordingly, parameters, e.g., constant C, for the calculation of distal tension $T_{DIST}$ in step 525 can generally be selected based on the assumption that the other actuator will apply the minimum tension $T_{MIN}$.

The principles described above for control of a single joint in a medical instrument can also be employed to simultaneously control multiple joints in an instrument. FIG. 6 schematically illustrates a multi jointed medical instrument 600 and some quantities used in control processes for instrument 600. Instrument 600 includes L joints 610-1 to 610-L, generically referred to herein as joints 610. Each joint 610 provides a range of relative positions or orientations of adjacent mechanical members and typically has one or two degrees of freedom of motion as described further below. Joints 610 of instrument 600 provide a total of N degrees of freedom, where the number N of degrees of freedom is greater than or equal to the number L of joints 610, and the configurations of degrees of freedom of joints 610 can be described using N-components or a vector θ. An N-component velocity vector $\dot{\theta}$ is associated with the vector θ. Torques $\tau_1$ to $\tau_N$, which move joints 610-1 to 610-L, respectively correspond to the N components of vector θ in that torques $\tau_1$ to $\tau_N$ tend to cause respective components of vector θ to change.

Joints 610 are actuated using M transmission systems 620-1 to 620-M (generically referred to herein as transmission systems 620) and M actuators 640-1 to 640-M (generically referred to herein as actuators 640). Transmission systems 620 and actuators 640 can be similar or identical to transmission systems 420 and actuators 440, which are described above with reference to FIG. 4. In general, the number M of transmission systems 620 and actuators 640 is greater than the number N of degrees of freedom, but the relationship between M and N depends on the specific medical instrument and the mechanics of joints in the instrument. For example, a joint 610 providing a single degree of freedom of motion may be actuated using two transmission systems 620, and a joint 610 providing two degrees of freedom may be actuated using three or four transmission systems 620. Other relationships between degrees of freedom and actuating transmission systems are possible. Control system 650 operates actuators 640-1 to 640-M to select respective tensions $T_1$ to $T_M$ that actuators 640-1 to 640-M respectively apply to transmission systems 620-1 to 620-M.

Control system 650 for instrument 600 can use one or more measurements representative of position and velocity vectors θ and $\dot{\theta}$ to determine position and velocity vectors θ and $\dot{\theta}$, e.g., to estimate position and velocity vectors θ and $\dot{\theta}$. In some cases, control system 650 for instrument 600 can use one or more sensors to determine position and velocity vectors θ and $\dot{\theta}$ and associated with joints 610. The one or more sensors can include a distal sensor (not shown) to determine position and velocity vectors θ and $\dot{\theta}$ associated with joints 610. (Position and velocity are used here to include the values and movement of linear or angular coordinates.) Alternatively control system 650 can use one or more proximal sensors associated with actuators 640 to determine position and velocity vectors θ and $\dot{\theta}$. Each actuator 640 can include a corresponding proximal sensor to generate measurements indicative of position and velocity vectors θ and $\dot{\theta}$. Proximal sensors can include, for example, encoders, tachometers, and other appropriate sensors to be coupled with actuators 640. In some cases, proximal sensors are sensors of instrument 600. Alternatively, proximal sensors are associated with actuators 640.

Control system 650 also determines a desired configuration of joints 610. The desired configuration can be indicative of desired position and velocity vectors $\theta_D$ and $\dot{\theta}_D$ of joints 610. As described further below, the desired position and velocity vectors $\theta_D$ and $\dot{\theta}_D$ depend on input from a manual controller 660 that may be manipulated by a surgeon using instrument 600. In general, the desired position and velocity vectors $\theta_D$ and $\dot{\theta}_D$ will further depend on the criteria or constraints, e.g., a set of values indicative of minimum tensions in transmission systems 620, a set of values indicative of maximum tensions in transmission systems 620, etc., defined in the control process implemented using control system 650.

FIG. 7 illustrates a control process 700 in accordance with an embodiment of the invention for controlling a multi jointed instrument such as instrument 600 of FIG. 6. Process 700 begins in step 710 by determining joint position vector θ from one or more sensors, e.g., associated with the instrument or coupled with actuators 640. The velocity vector $\dot{\theta}$ can also be determined, for example, using a direct measurement of joint movement or through calculation of the change in position measurements between two times.

In some examples, positions of actuators 640 can be considered to be mechanically coupled to positions of joints 610. In step 710, position vector θ can be determined based on actuator position vector $\theta_A$ having elements corresponding to respective positions of actuators 640. Each position component $\theta_i$, for an index i from 1 to N is determined using Equation 2, which defines a system of equations defining the relationship between actuator positions and joint positions. In Equation 2, $\theta_1$ to $\theta_N$ are components of the position vector θ of joints 610, and $\theta_{A1}$ to $\theta_{AM}$ are components of the position vector $\theta_A$ respectively in M actuators 640 that articulate joints 610. Each coefficient $b_{IJ}$ for index I=1 to N and index J=1 to M generally corresponds to a coupling constant between an actuator J and a joint I. For example, a unit coupling constant for $b_{IJ}$ for a given I and a given J indicates that the position of joint I is considered to be directly proportional to the position of actuator J. The matrix with components $b_{IJ}$ can be referred to as coupling matrix C.

$$\begin{bmatrix} \theta_1 \\ \theta_2 \\ \vdots \\ \theta_N \end{bmatrix} = \begin{bmatrix} b_{11} & \cdots & b_{1M} \\ \vdots & \ddots & \vdots \\ b_{N1} & \cdots & b_{NM} \end{bmatrix} \begin{bmatrix} \theta_{A1} \\ \theta_{A2} \\ \vdots \\ \theta_{AM} \end{bmatrix} \quad \text{Equation 2}$$

Control system 650 receives a surgeon's instructions in step 715. The surgeon's instructions can indicate a desired configuration of the instrument, e.g., specifying a position and velocity of a specific working portion of the instrument. For example, a surgeon through manipulation of manual control 660 can indicate a desired position, velocity, orientation, and rotation of the distal tip or end effector of the instrument such as described in U.S. Pat. No. 6,493,608, entitled "Aspects of a Control System of a Minimally Invasive Surgical Apparatus," which is incorporated herein by reference.

Step 720 then converts the instructions from manual controller 660 into desired position and velocity vectors $\theta_D$ and $\dot{\theta}_D$ for joints 610. For example, given the desired position, orientation, velocity, and angular velocity of the distal tip of instrument 600 of FIG. 6, control system 650 can calculate desired joint position and velocity vectors $\theta_D$ and $\dot{\theta}_D$ that will achieve the desired tip configuration. The conversion step 720 can be achieved with well-known techniques, such as differential kinematics inversion as described by "Modeling and Control of Robot Manipulators," L. Sciavicco and B. Siciliano, Springer, 2000, pp.

104-106 and "Springer Handbook of Robotics," Bruno Siciliano & Oussama Khatib, Editors, Springer, 2008, pp. 27-29, which are incorporated herein by reference. Above-referenced U.S. Pat. No. 6,493,608, entitled "Aspects of a Control System of a Minimally Invasive Surgical Apparatus," also describes techniques for determining desired joint position and velocity vectors $\theta_D$ and $\dot{\theta}_D$ that will achieve the desired tip configuration. It should be noted that for instruments with a kinematic redundancy, i.e., if the number of degrees of freedom of motion provided by joints 610 is larger than the number of degrees of freedom of the motion command specified by manual controller 660, the redundancy can be resolved with standard techniques such as those described in Yoshihiko Nakamura, "Advanced Robotics: Redundancy and Optimization," Addison-Wesley (1991).

It should also be appreciated that software enforced constraints between the joints of the instruments can also be enforced when solving the inverse kinematics problem on the desired command for the instrument. For instance, the joint positions and velocity commands of two joints can be forced to be the same or opposite or in a given ratio, effectively implementing a virtual cam mechanism between the joints. The software enforced constraints can include software enforced minimum tensions in the transmission systems of the instrument, maximum tensions in the transmission systems of the instrument, etc. The software enforced constraints can be dynamically enforced during a surgical procedure. As desired positions, desired velocities, measured positions, and measured velocities vary, the software enforced constraints can vary.

Step 725 computes a position error vector $(\theta_D-\theta)$ and velocity error vector $(\dot{\theta}_D-\dot{\theta})$, and step 730 uses components of error vectors $(\theta_D-\theta)$ and $(\dot{\theta}_D-\dot{\theta})$, for calculation of respective torque components $\tau_1$ to $\tau_N$. In one specific embodiment, each torque component $\tau_i$ for an index i from 1 to N is determined using Equation 3. In Equation 3, $g1_i$ and $g2_i$ are gain factors, and $C_i$ is a constant or geometry-dependent parameter that may be selected according to known or modeled forces applied to the joint by other portions of the system. However, parameter $C_i$ is not required to strictly be a constant but could include non-constant terms that compensate for properties such as gravity or mechanism stiffness that can be effectively modeled, and accordingly, $C_i$ may depend on the measured position or velocity of the joint 610-i on which the torque $\tau_i$ acts. In general, gain factors $g1_i$ and $g2_i$ and constant $C_i$ can be selected according to the desired stiffness and dampening or responsiveness of a joint or according to an accumulation of error. For example, when inserting the instrument 600 to follow a natural lumen within a patient, the gain factor $g1_i$ can be set to a low value to make a joint behave gently and prevent the joint action from harming surrounding tissue. After the insertion, the gain factor $g1_i$ can be set to a higher value that allows the surgeon to perform a precise surgical task with the instrument. Other equations or corrections to Equation 3 could be employed in the determination of the torque. For example, the calculated torque could include a correction proportional to a saturated integral of the difference between the current measurement of joint position and the desired joint position that the previously applied torque was intended to achieve. Such correction using a saturated integral could be determined as described above for the single joint control process of FIG. 5A and particularly illustrated by steps 530 and 535 of FIG. 5A.

$$\tau_i = g1_i(\theta_D-\theta)_i + g2_i(\dot{\theta}_D-\dot{\theta})_i + C_i \qquad \text{Equation 3:}$$

Step 735 uses the torques computed in step 730 to determine distal tensions $T_{DIST}$. Distal tension $T_{DIST}$ is an M component vector corresponding to transmission systems 620-1 to 620-M and actuators 640-1 to 640-M. The determination of the distal tensions depends on geometry or mechanics between the instrument joints and transmission systems. In particular, with multiple joints, each joint may be affected not only by the forces applied directly by transmission systems attached to the joint but also by transmission systems that connect to joints closer to the distal end of the instrument. The torques and tensions in a medical instrument can generally be modeled using equations of the form of Equation 4. In Equation 4, $\tau_1$ to $\tau_N$ are components of the torque vector, and $T_1$ to $T_M$ are the distal tensions respectively in M transmission systems 620 that articulate joints 610. Each coefficient au for index I=1 to N and index J=1 to M generally corresponds to the effective moment arm of the tension $T_J$ for joint and rotation axis corresponding to torque $\tau_1$.

$$\begin{bmatrix} \tau_1 \\ \tau_2 \\ \vdots \\ \tau_N \end{bmatrix} = \begin{bmatrix} a_{11} & a_{12} & \cdots & a_{1M} \\ a_{21} & a_{22} & \cdots & a_{2M} \\ \vdots & \vdots & \ddots & \vdots \\ a_{N1} & a_{N2} & \cdots & a_{NM} \end{bmatrix} \begin{bmatrix} T_1 \\ T_2 \\ \vdots \\ T_M \end{bmatrix} = A \begin{bmatrix} T_1 \\ T_2 \\ \vdots \\ T_M \end{bmatrix} \qquad \text{Equation 4}$$

The computation in step 735 thus corresponds to solving N equations for M variables $T_1$ to $T_M$. Since M is generally greater than N, the solution is not unique, so that inequality constraints can be selected, such as the constraint that all tensions are greater than a set of minimum values, and optimality conditions, such as the condition that a set of tensions of lowest maximum value is chosen, can be applied to provide a unique solution with desired characteristics such as minimal tensions that stay above a desired threshold in all or selected joints. The matrix inversion problem of Equation 4 with inequality and optimality constraints such as minimal tension constraints can be solved by some well-known techniques such as the SIMPLEX method of linear programming. (See, e.g., "Linear Programming 1: Introduction," George B. Dantzig and Mukund N. Thapa, Springer-Verlag, 1997, which is incorporated herein by reference in its entirety.) In accordance with a further aspect of the invention, the distal tensions can be determined using a process that sequentially evaluates joints beginning with the most distal joint and solves for tensions in transmission systems that connect to each joint based on geometric parameters and the tensions previously calculated for more distal joints.

In some cases, the distal tensions $T_1$ to $T_M$ to be applied are directly proportional to actuator torques $\tau_{A1}$ $\tau_{AN}$ to $T_{AN}$ to be applied by actuators 640. In this regard, in some cases, at step 735, actuator torques $T_{A1}$ to $T_{AN}$ are determined. In Equation 5 ($\tau_A = D\tau$), each coefficient $d_{JI}$ of coupling matrix D for index I=1 to N and index J=1 to M generally corresponds to the torque coupling between a joint I and an actuator J. If position vector $\theta$ of joints 610 is determined based on Equation 2, the relationship between torques $\tau_1$ to $T_N$ (represented by torque vector $\tau$) and torques $\tau_{A1}$ to $\tau_{AM}$ (represented by torque vector $\tau_A$) to be applied by actuators 640 can be determined based on the coupling matrix C. Coupling matrix D relating the torque vector $\tau$ and the torque vector $\tau_A$ can be equal to the transpose of coupling matrix C. With Equation 5, at step 735, the torques $\tau_{A1}$ to $\tau_{AM}$ to be applied to actuators 640 can be determined given joint torques $\tau_1$ to $\tau_N$, for example, calculated using Equation 3.

$$\begin{bmatrix} \tau_{A1} \\ \tau_{A2} \\ \vdots \\ \tau_{AM} \end{bmatrix} = \begin{bmatrix} d_{11} & \cdots & d_{1N} \\ \vdots & \ddots & \vdots \\ d_{M1} & \cdots & d_{MN} \end{bmatrix} \begin{bmatrix} \tau_1 \\ \tau_2 \\ \vdots \\ \tau_N \end{bmatrix} \quad \text{Equation 5}$$

Control system 650 in one embodiment of process 700 activates actuators 640. As described with respect to step 735, distal tensions to be applied to transmission system 620 or torques to be applied to actuators 640 can be determined. Actuators 640 can be activated to apply the distal tensions or the torques calculated in step 735 to respective transmission systems 620.

Alternatively, corrections to the distal tensions can be determined as illustrated by steps 740 and 745. In particular, step 740 computes a correction tension $T_{PROX}$, which depends on the difference between a desired transmission velocity vector $\dot{\theta}_{DL}$, computed based on desired joint velocity $\dot{\theta}_D$, and a current transmission velocity vector $\dot{\theta}_L$, computed based on the current actuator velocity $\dot{\theta}_A$. In one particular embodiment, the desired transmission velocity can be the multiplication of the transpose of the coupling matrix A in Equation 4 with the desired joint velocity $\dot{\theta}_D$, while the current transmission velocity can be the product of the actuator velocity $\dot{\theta}_A$ and respective moment arm of actuators 640. Correction tension $T_{PROX}$ can compensate for inertia or other effects between the actuator 640 and the connected joint 610 and, in one embodiment, is a function of the difference $(\dot{\theta}_{DL} - \dot{\theta}_L)$ such as the product of difference $(\dot{\theta}_{DL} - \dot{\theta}_L)$ and a gain factor. Step 745 computes a correction tension $T_{PAIR}$, which depends upon a difference or differences between the velocities of actuators that actuate the same joint. For example, in the case in which a joint provides one degree of freedom of motion and is actuated by a pair of actuators connected to the joint through a pair of transmission systems, correction tension $T_{PAIR}$ can be determined as a function of the difference between the velocities of the two actuators. (See, for example, step 550 of FIG. 5A as described above.) Corrections similar to correction tension $T_{PAIR}$ can be generalized to the case where three or more transmission systems and actuators actuate a joint having two degrees of freedom of motion.

Step 750 combines distal tension $T_{DIST}$ and any corrections $T_{PROX}$ or $T_{PAIR}$ to determine a combined tension T applied by the actuators. In general, each component $T_1$ to $T_M$ of the combined tension T can be limited to saturate at a maximum tension $T_{MAX}$ or a minimum tension $T_{MIN}$ if the sum of the calculated distal tensions $T_{DIST}$ and corrections $T_{PROX}$ and $T_{PAIR}$ is greater than or less than the desired maximum or minimum values as described above with reference to FIG. 5D. As a result, all tensions $T_1$ to $T_M$ are no less than a minimum tension $T_{MIN}$ or no greater than a maximum tension $T_{MAX}$. Steps 755 and 760 then activate actuators 640 to apply and hold the combined tension T for a time interval $\Delta t$ before process 700 returns to step 710 and reads the new joint positions. Holding the tension for an interval of roughly 4 ms or less, which corresponds to a rate of 250 Hz or higher, can provide smooth movement of an instrument for a medical procedure. In some implementations, time interval $\Delta t$ is 0.1 ms to 4 ms, e.g., 0.1 ms to 1 ms, 1 ms to 2 ms, 2 ms to 3 ms, or 3 ms to 4 ms.

Medical instruments commonly require that the working tip or end effector of the instrument have a position and orientation that an operator such as a surgeon can control. On the other hand, the specific position and orientation of each joint is generally not critical to the procedure being performed, except where joint position or orientation is mandated by the lumen through which the instrument extends.

In accordance with an aspect of the invention, one approach to control a multi joint instrument selects tensions applied through tendons using differences between current and desired configurations of an end portion of an instrument, e.g., such as an end effector, a tip, or other movable device. For example, differences between the measured position, orientation, velocity, and angular velocity of the end portion of the instrument and the desired position, orientation, velocity, and angular velocity of the end portion of the instrument can control the tensions applied to tendons of a medical instrument. FIG. 7B illustrates a control process 700B in accordance with an embodiment of the invention.

Figure 7A:
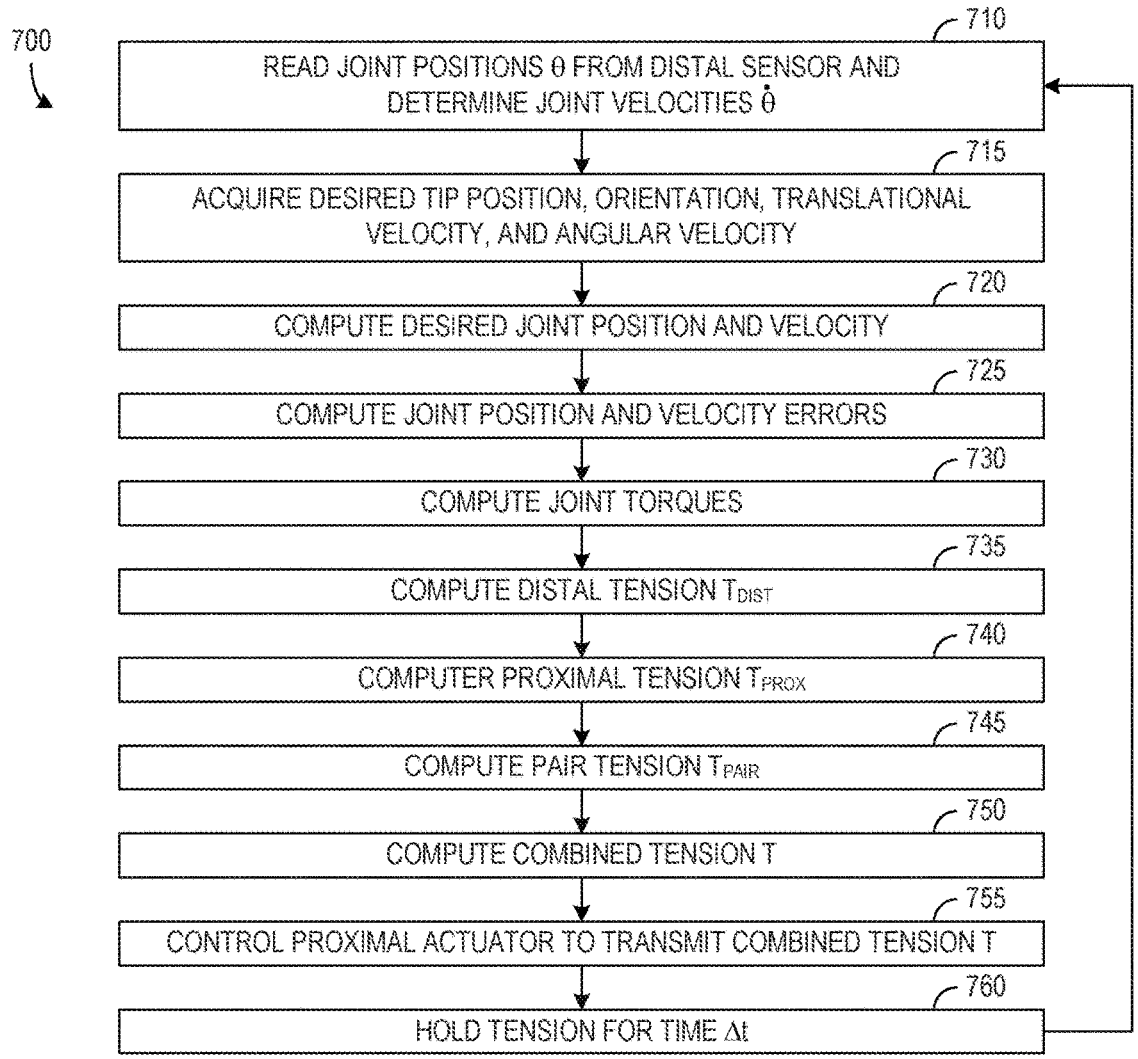
FIG. 7A is a flow diagram of a process in accordance with an embodiment of the invention that selects applied tensions based on differences between measured and desired joint configurations.
Figure 7B:
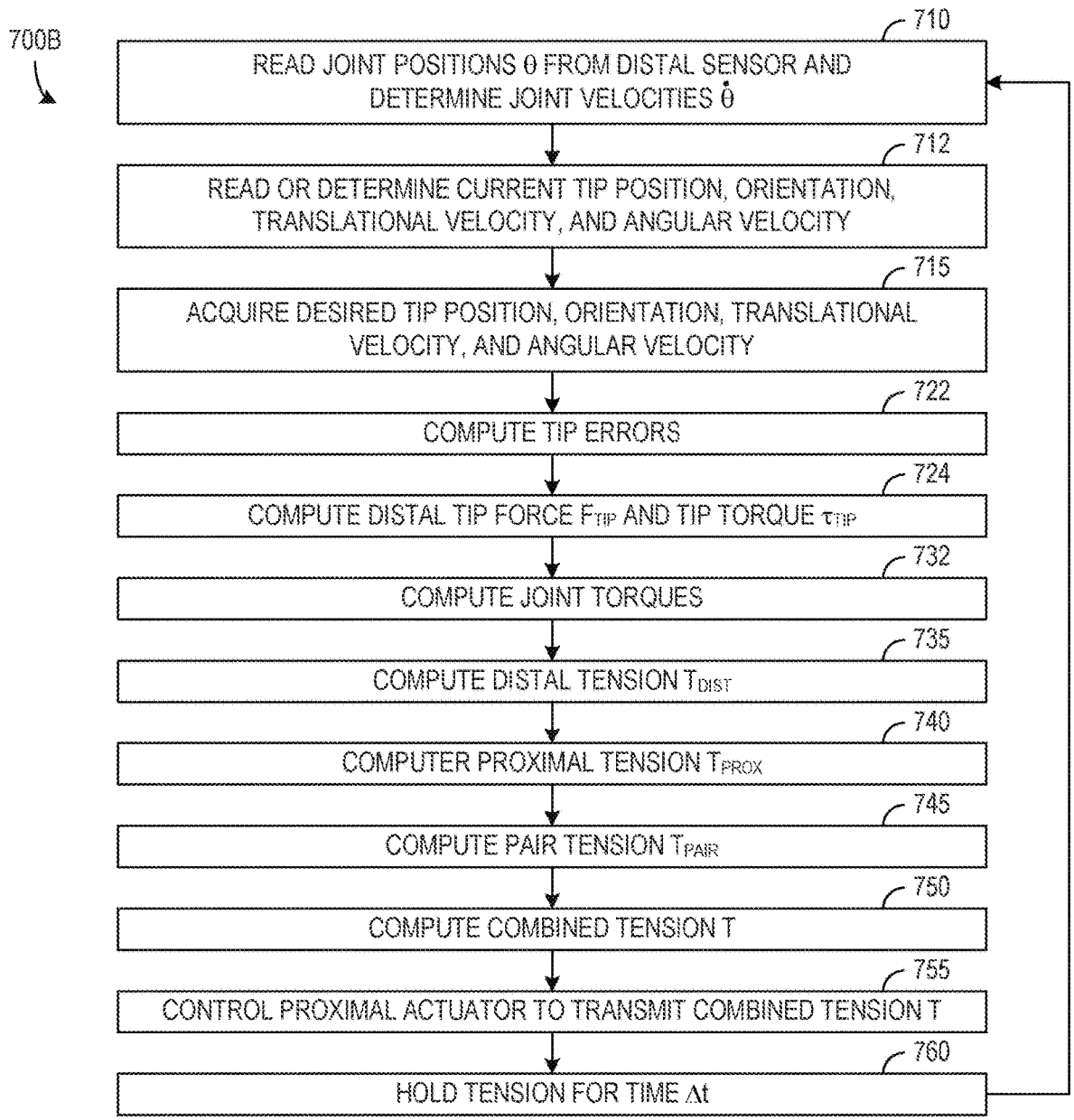
FIG. 7B is a flow diagram of a process in accordance with an embodiment of the invention that selects applied tensions based on differences between measured and desired tip configurations.

Process 700B employs some of the same steps as process 700, and those steps have the same reference numbers in FIGS. 7A and 7B. Process 700B in step 710 determines the joint positions $\theta$ and joint velocities $\dot{\theta}$, for example, from a sensor or sensors. As described herein, the sensor or sensors can include distal sensors or proximal sensors. In step 712, process 700B reads or determines a position, orientation, velocity, and angular velocity of a tip of the instrument. Tip here refers to a specific mechanical structure in the instrument and may be an end effector such as forceps, scissors, a scalpel, or a cauterizing device on the distal end of the instrument. In some examples, an end portion of the instrument includes the tip. In general, the tip has six degrees of freedom of motion and has a configuration that can be defined by six component values, e.g., three Cartesian coordinates of a specific point on the tip and three angles indicating the pitch, roll, and yaw of the tip. Velocities associated with changes in the configuration coordinates over time may be directly measured or calculated using measurements at different times. Given joint positions and velocities $\theta$ and $\dot{\theta}$ and a priori knowledge of the kinematic model of the instrument 600, one can build both forward and differential kinematic models that allow computing the Cartesian position, orientation, translational velocity, and angular velocity of the tip with respect to the frame of reference of the instrument 600. The forward and differential kinematic model of a kinematic chain can be easily constructed according to known methods. For instance, the procedure described by John J. Craig, "Introduction to Robotics: Mechanics and Control," Pearson Education Ltd. (2004), which is incorporated herein by reference, may be used. Step 715 determines the desired tip position, orientation, translational velocity, and angular velocity, which can be performed in the manner described above. The desired tip position, orientation, translational velocity, and angular velocity may be computed using kinematic models similar to those described herein with respect to computing configurations of instrument 600.

In another embodiment, a sensor, for example, a shape sensor, may be used to directly measure Cartesian position and orientation as described in U.S. Pat. App. Pub. No. 20090324161 entitled "Fiber optic shape sensor" by Giuseppe M. Prisco, which is incorporated herein by reference. Translational velocities associated with changes in the configuration coordinates over time may be calculated using measurements at different times. Unlike the translational velocities, the angular velocities cannot be computed simply by the differencing approach due to the angular nature of the quantities. However, the methods of computing the angular velocities associated with the changes in orientation are known in the art and described, for example, by L. Sciavicco and B. Siciliano, "Modelling and Control of Robot Manipulators," Springer 2000, pp. 109-111.

Process 700B in step 722 calculates tip errors. The tip errors are indicative of a difference between a current configuration of the tip and a desired configuration of the tip. In one embodiment, step 722 includes calculating a position error or difference epos between the desired Cartesian coordinates of the tip and the current Cartesian coordinates of the tip, a translational velocity error or difference $e_{VT}$ between the desired translational velocity of the tip and the current translational velocity of the tip, an orientation error or difference $e_{ORI}$ between the desired orientation coordinates of the tip and the current orientation coordinates of the tip, and an angular velocity error or difference $e_{VA}$ between the desired angular velocity of the tip and the current angular velocity of the tip. Unlike the position error $e_{POS}$, the orientation error $e_{ORI}$ cannot be computed simply by the differencing approach due to the angular nature of the quantities. However, the methods of computing the change in orientation are known in the art and can be found in robotics literatures, for example, L. Sciavicco and B. Siciliano, "Modelling and Control of Robot Manipulators," Springer, 2000, pp. 109-111.

In step 724, process 700B determines a tip force $F_{TIP}$ and a tip torque $\tau_{TIP}$ that are intended to move tip from the current configuration to the desired configuration. In this embodiment of the invention, tip force $F_{TIP}$ depends on errors $e_{POS}$ and $e_{VT}$. For example, each component $F_X$, $F_Y$, or $F_Z$ of tip force $F_{TIP}$ can be calculated using Equation 6, where $gp_i$ and $gv_i$ are gain factors and $Cf_i$ is a constant. The tip torque $\tau_{TIP}$ can be determined in a similar manner, in which each component of tip torque $\tau_i$ is a function of errors $e_{ORI}$ and $e_{VA}$ with another set of gain factors and constants $gori_i$, $gva_i$, and $C\tau_i$ as shown in Equation 7. In general, the gain factors $gp_i$ and $gv_i$ associated with different force or torque components $F_i$ and $\tau_i$ can be different. Having separate gain factors and constants for each component of tip force $F_{TIP}$ and tip torque $\tau_i$ provides flexibility in specifying the dynamic behavior of the end effector or instrument tip, enhancing more effective instrument interaction with the tissue. For instance, when navigating the instrument into a small lumen, one may set low values for the gain factors of tip force perpendicular to the inserting direction while have high values for the gain factors along the inserting direction. With that, the instrument is sufficient stiff for insertion while having low lateral resistance to the tissue, preventing damage to the surrounding tissue. Another example, when using the instrument to punch a hole in the tissue in certain direction, having high values in the gain factors of the tip torque as well as the gain factor along the inserting direction of the tip force, facilitate the hole-punch task.

$$F_i = gp_i * e_{POS} + gv_i * e_{VT} + Cf_i \qquad \text{Equation 6:}$$

$$\tau_i = gori_i * e_{ORI} + gva_i * e_{VA} + C\tau_i \qquad \text{Equation 7:}$$

Step 732 determines a set of joint torques that will provide the tip force $F_{TIP}$ and tip torque $\tau_{TIP}$ determined in step 724. The relationships between joint torque vector $\tau$, tip force $F_{TIP}$, and tip torque $\tau_{TIP}$ are well-documented and normally described as in Equation 8, where $J^T$ is the transpose of the well-known Jacobian Matrix J of a kinematic chain of the instrument.

$$\tau = J^T \begin{bmatrix} F_{TIP} \\ \tau_{TIP} \end{bmatrix} \qquad \text{Equation 8}$$

The Jacobian Matrix J depends on the geometry of the instrument and the current joint positions determined in step 710 and can be constructed using known methods. For example, John J. Craig, "Introduction to Robotics: Mechanics and Control," Pearson Education Ltd. (2004), which is incorporated herein by reference, describes techniques that may be used to construct the Jacobian Matrix for a robotic mechanism. In some cases, if there are extra or redundant degrees of freedom of motion provided in the medical instrument, e.g., more than the six degrees of freedom of motion of the tip, the set of joint torques that provides tip force $F_{TIP}$ and tip torque $\tau_{TIP}$ is not unique, and constraints can be used to select a set of joint torques having desired properties, e.g., to select a set of joint torques that prevents the joints reaching their mechanical joint limits in range of motion or supported loads or to enforce extra utility on any particular joints of the instrument during manipulation. For instance, one can prevent the joints reaching their mechanical joint limits by selecting a set of joint torques that minimizes the deviation from the midrange joint positions, from the null space associated with the transpose of Jacobian matrix $J^T$. The set of joint torques can be selected according to Equation 9. In Equation 9, $P(\theta)$ is a potential function that define addition utility to be provided by the solution, $\nabla$ is a gradient operator, $N(\ )$ is a null space projection operator that selects a set of joint torques from the null space of the transpose of Jacobian matrix $J^T$, associated with its input. In one embodiment, potential $P(\theta)$ a quadratic function of the joint positions that has a minimum when the joints are in the center of their range of motion. The gradient of the potential function $-\nabla P(\theta)$ selects a set of joint torques that draws joints moving toward the center of their range of motion while the null space projection operator $N(\ )$ enforces that the selected set of joint torques providing the desired tip force and tip torques also satisfy the additional utility. Techniques for using constraints in robotic systems providing redundant degrees of freedom of motion are known in the art and can be found in robotics literatures. See, for instance, Yoshihiko Nakamura, "Advanced Robotics: Redundancy and Optimization," Addison-Wesley (1991) and literature by Oussama Khatib, "The Operational Space Framework," JSME International Journal, Vol. 36, No. 3, 1993.

$$\tau = J^T \begin{bmatrix} F_{TIP} \\ \tau_{TIP} \end{bmatrix} + N(-\nabla P(\theta)) \qquad \text{Equation 9}$$

Process 700B after step 732 proceeds in the same manner as process 700 described above. In particular, based on the joint torques determined in step 732, step 735 determines tensions $T_{DIST}$. Steps 740 and 745 determine corrections $T_{PROX}$ and $T_{PAIR}$ to tensions $T_{DIST}$, and step 750 determines a combined tension vector T. Steps 755 and 760 then apply and hold the components of combined tension vector T on the transmission systems to actuate the medical instrument during a time interval $\Delta t$.

Processes 700 and 700B of FIGS. 7A and 7B required determination of tensions that will produce a particular set of joint torques. The tendon tension for a single isolated joint can be determined from a joint torque simply by dividing the joint torque by the moment arm at which the tension is applied. In the multi joint case, due to geometry of the transmission system and cable routing and redundancy in the actuation cable, the problem amounts to solving a system of equations with constraints. In one particular embodiment, one may apply non-negative tendon tension constraints (or minimum tension constraints) when solving the system of equations to prevent slacking in the cables or other tendons in the transmission systems. The inputs of the problem are the determined joint torque for each joint while the geometry of cable routing defines the system of equations (or the coupling matrix A of Equation 4). Appropriate tendon tensions are needed that fulfill Equation 4 and are larger than minimum tension constraints.

In some examples, a standard optimization method, called SIMPLEX method can be used to handle this matrix inverse problem with inequality and optimality constraints. The SIMPLEX method can require a relatively larger computation time and may not be advantageous to be used in real time application. Also, the SIMPLEX method does not guarantee continuity in the solutions as the joint torques change. To speed-up the computation efficiency and provide a continuous output solution, an iterative approach can be considered which relies on the triangular nature of the coupling matrix A. FIGS. 8A, 8B, 8C, 9A, 9B, 9C, 9D, and 9E illustrate a few specific examples of joints in multi jointed instruments and are used herein to illustrate some properties of the coupling matrix A in Equation 4.

Various constraints can be enforced using the optimization methods described herein. If the number of actuators M is greater than the number of joints N, one of the redundant degrees of freedom of instrument 600 can be utilized to enforce a minimum tension $T_{MIN}$. In some examples, a minimum tension $T_{MIN}$ can be enforced such that the tension in each of each transmission system 620 is greater than or equal to minimum tension $T_{MIN}$. Torques $\tau_{A1}$ to $\tau_{AM}$ to be applied can be selected to enforce minimum tension $T_{MIN}$ in each transmission system 620. In this regard, the actuator torques $\tau_{A1}$ to $\tau_{AM}$ can each be biased by a certain amount of tension to achieve such tensions above minimum tension $T_{MIN}$. Actuators 640 can be controlled to apply tensions to transmission systems 620 both based on the position and velocity errors and based on offset tensions that cause the applied tensions to be no less than minimum tension $T_{MIN}$. This can inhibit slack in transmission systems 620, e.g., during a surgical procedure, thereby improving responsiveness of instrument 600.

In some examples, offset tensions are provided by a parameter that is independent of positions of joints 610 so that variation in the parameter does not influence net torques on joints 610 and thus does not influence positioning of joints 610. The parameter is dependent on positions of actuators 640. As a result, actuators 640 can be driven to maintain a particular value for the parameter or a particular range of values for the parameter without affecting joint torques. If actuators 640 are controlled based on determined torques $\tau_{A1}$ to $\tau_{AM}$, a bias parameter τBIAS can be selected to offset torques applied by actuators 640 and hence to offset tensions applied to transmission systems 620. Bias parameter $\tau_{BIAS}$ thus provides the offset tensions applied to transmission systems 620. Absent bias parameter $\tau_{BIAS}$ (e.g., when bias parameter τBIAS is equal to zero), resulting baseline tensions applied to transmission systems 620 are based only on position errors of joints 610 and not based on the offset tensions or other constraint-based tensions. With a non-zero value for bias parameter $\tau_{BIAS}$, resulting tensions applied to transmission systems 620 are based on position errors of joints 610 and based on the offset tensions.

A selected bias parameter $\tau_{BIAS}$ can provide a corresponding offset tension for each of tensions $T_1$ to $T_M$. For example, in some cases, multiple offset tensions are equal to one another. Alternatively or additionally, multiple offset tensions are different from one another. In some cases, all of the offset tensions are equal to one another, and in other cases, none of the offset tensions are equal to one another.

By way of example, bias parameter $\tau_{BIAS}$ can form part of a system of equations to provide the offset tensions. The system of equations, including equations relating joint positions and actuator positions, is augmented to include an additional equation that functions as a constraint on tensions $T_1$ to $T_M$ of transmission systems 620. This additional equation provides the offset tensions that bias the applied tensions $T_1$ to $T_M$ to be no less than minimum tension $T_{MIN}$. For example, this additional equation is defined by a relationship between $\theta_T$ representing a tension degree of freedom (in Equation 2A below) and actuator positions $\theta_{A1}$ to $\theta_{AM}$. While $\theta_1$ to $\theta_N$ correspond to physical positions of joints 610, $\theta_T$ corresponds not to a physical position of a joint but rather a tension degree of freedom $\theta_T$ that is adjustable to cause corresponding tensions in transmission systems 620. Equation 2A ($\theta = C\theta_A$) corresponds to Equation 2 augmented by an additional equation usable to enforce minimum tension $T_{MIN}$, as represented by coefficients $b_{T1}$ to $b_{TM}$ and variable $\theta_T$. The matrix C corresponds to the full matrix of Equation 2 with additional coefficients $b_{T1}$ to $b_{TM}$ for tension degree of freedom $\theta_T$. Components of matrix C are selected such that at least one column is linearly independent of the others, e.g., the column corresponding to the tension degree of freedom $\theta_T$. This linear independence can ensure that enforcement of the minimum tension constraint does not cause corresponding changes to positions of the joints or a net torque applied to the joints. For example, the linear independence ensures that positions $\theta_1$ to $\theta_N$ remain unchanged in response to changes in the tension degree of freedom $\theta_T$.

$$\begin{bmatrix} \theta_1 \\ \theta_2 \\ \vdots \\ \theta_N \\ \theta_T \end{bmatrix} = \begin{bmatrix} b_{11} & \cdots & b_{1M} \\ \vdots & \ddots & \vdots \\ b_{N1} & & b_{NM} \\ & \cdots & \\ b_{T1} & & b_{TM} \end{bmatrix} \begin{bmatrix} \theta_{A1} \\ \theta_{A2} \\ \vdots \\ \theta_{AM} \end{bmatrix} \quad \text{Equation 2A}$$

The relationship between actuator torques $\tau_{A1}$ to $\tau_{AM}$ to be applied and joint torques $\tau_1$ to $\tau_N$ can be represented by Equation 5A. As described above, matrix D having coefficients $d_{11}$ to $d_{MN}$ for index I=1 to N and index J=1 to M can be determined by taking the transpose of coupling matrix C of Equation 2A. The bias parameter $\tau_{BIAS}$ can be selected to provide offset tensions that cause each of actuator torques $\tau_{A1}$ to $\tau_{AM}$ to be applied to be greater than minimum torque $\tau_{MIN}$, e.g., corresponding to minimum tension $T_{MIN}$.

As shown in Equation 5A, applied actuator torques $\tau_{A1}$ to $\tau_{AM}$ can be equal to the sum of baseline torques and bias torques. The baseline torques correspond to the torques to be applied to actuators 640 absent the minimum tension constraint. Both the baseline torques and applied actuator torques $\tau_{A1}$ to $\tau_{AM}$ result in tensions applied to transmission systems 620 that reduce the difference between the current configuration and the desired configuration. Said another way, the baseline torques and actuator torques $\tau_{A1}$ to $\tau_{AM}$, when applied, generate a desired net torque at joints 610. The bias torques correspond to the additional torques to be applied to actuators 640 to ensure that actuator torques $\tau_{A1}$ to $\tau_{AM}$ is each greater than minimum torque $T_{MIN}$. The bias torques do not influence the current configuration. Said another way, the bias torques, when applied to transmission systems 620, provide the offset tensions to transmission systems 620 and generate a zero net torque at joints 610. The bias torques provide offset tensions to transmissions systems 620 such that an average of the tensions experienced by transmission systems 620 is maintained. Accordingly, the net torque on joints 610 is not affected by the offset tensions.

In some examples, using Equation 5A, bias parameter $\tau_{BIAS}$ can be the minimum value required such that each of torques $\tau_{A1}$ to $\tau_{AM}$ is greater than minimum torque $\tau_{MIN}$. In an example of a process to select a minimum value of bias parameter $\tau_{BIAS}$, for each actuator torque $\tau_{A1}$ to $\tau_{AM}$, an offset torque added to the baseline torque is determined. For each actuator torque $\tau_{A1}$ to $\tau_{AM}$, the corresponding offset torque is determined so that the actuator torque is greater than minimum torque $\tau_{MIN}$. A maximum of these added torques is used to determine bias parameter $\tau_{BIAS}$ such that each of torques $\tau_{A1}$ to $\tau_{AM}$ is greater than minimum torque $\tau_{MIN}$. This ensures that bias parameter $\tau_{BIAS}$ is its minimum required value to enforce the minimum tension and torque constraint. As a result, by enforcing minimum torque $\tau_{MIN}$, one or more of torques $\tau_{A1}$ to $\tau_{AM}$ is equal to minimum torque $\tau_{MIN}$, and a remaining of torques $\tau_{A1}$ to $\tau_{AM}$ is greater than minimum torque $\tau_{MIN}$. In some cases, multiple torques of torques $\tau_{A1}$ to $\tau_{AM}$ are equal to minimum torque $\tau_{MIN}$. In particular, torques $\tau_{A1}$ to $\tau_{AM}$ are selected to inhibit slack in all of the transmission systems 620 and to maintain tensions in transmission systems 620 above minimum tension $T_{MIN}$.

$$\begin{bmatrix} \tau_{A1} \\ \tau_{A2} \\ \vdots \\ \tau_{AM} \end{bmatrix} = \begin{bmatrix} d_{11} & \cdots & d_{1N} & d_{1T} \\ \vdots & \ddots & \vdots & \vdots \\ d_{M1} & \cdots & d_{MN} & d_{MT} \end{bmatrix}_{baseline} \begin{bmatrix} \tau_1 \\ \tau_2 \\ \vdots \\ \tau_N \\ 0 \end{bmatrix} + \begin{bmatrix} d_{11} & \cdots & d_{1N} & d_{1T} \\ \vdots & \ddots & \vdots & \vdots \\ d_{M1} & \cdots & d_{MN} & d_{MT} \end{bmatrix}_{bias} \begin{bmatrix} 0 \\ 0 \\ \vdots \\ 0 \\ \tau_{BIAS} \end{bmatrix}$$

Equation 5A

In some implementations, bias parameter $\tau_{BIAS}$ is dynamically varied during the surgical procedure as the required bias torques to achieve tensions no less than minimum tension $T_{MIN}$ vary due to changes in desired and measured positions, velocities, and/or torques of the joints 610 and actuators 640. In this regard, bias parameter $\tau_{BIAS}$ can be varied at each measurement interval. When bias parameter $\tau_{BIAS}$ is dynamically varied, while tensions in transmission systems 620 may vary between measurement intervals, an average of tensions in transmission systems 620, e.g., a mean of the tensions in transmission systems 620, is maintained between different measurement intervals. The bias torques provide offset tensions to transmissions systems 620 such that the average of the tensions experienced by transmission systems 620 is maintained.

Torques $\tau_{A1}$ to $\tau_{AM}$, adjusted by bias parameter $\tau_{BIAS}$, are applied to generate corresponding tensions $T_1$ to $T_M$ in transmission systems 620. Values of each of tensions $T_1$ to $T_M$ can increase due to increases in bias parameter $\tau_{BIAS}$. As a result, adjustment of actuator torques $\tau_{A1}$ to $\tau_{AM}$ using bias parameter $\tau_{BIAS}$ can result in higher tensions $T_1$ to $T_M$. Even if bias parameter $\tau_{BIAS}$ is selected to be its minimum required value, bias parameter $\tau_{BIAS}$ may continue to increase due to slack in one transmission system, thereby causing high values for tensions for other transmission systems. For example, to achieve a desired configuration of joints 610, a first of transmission systems 620 can be driven to a higher value of tension while a second of transmission systems 620 is released to a lower value of tension. The tension in the second transmission system 620 can decrease to an extent that, in implementations in which bias parameter $\tau_{BIAS}$ is dynamically controlled, bias parameter $\tau_{BIAS}$ is increased to maintain the tension in the second transmission system 620 above the minimum tension $T_{MIN}$. As a result, the first transmission system 620 may experience increases in tension due to the increase in bias parameter $\tau_{BIAS}$.

Figure 11:
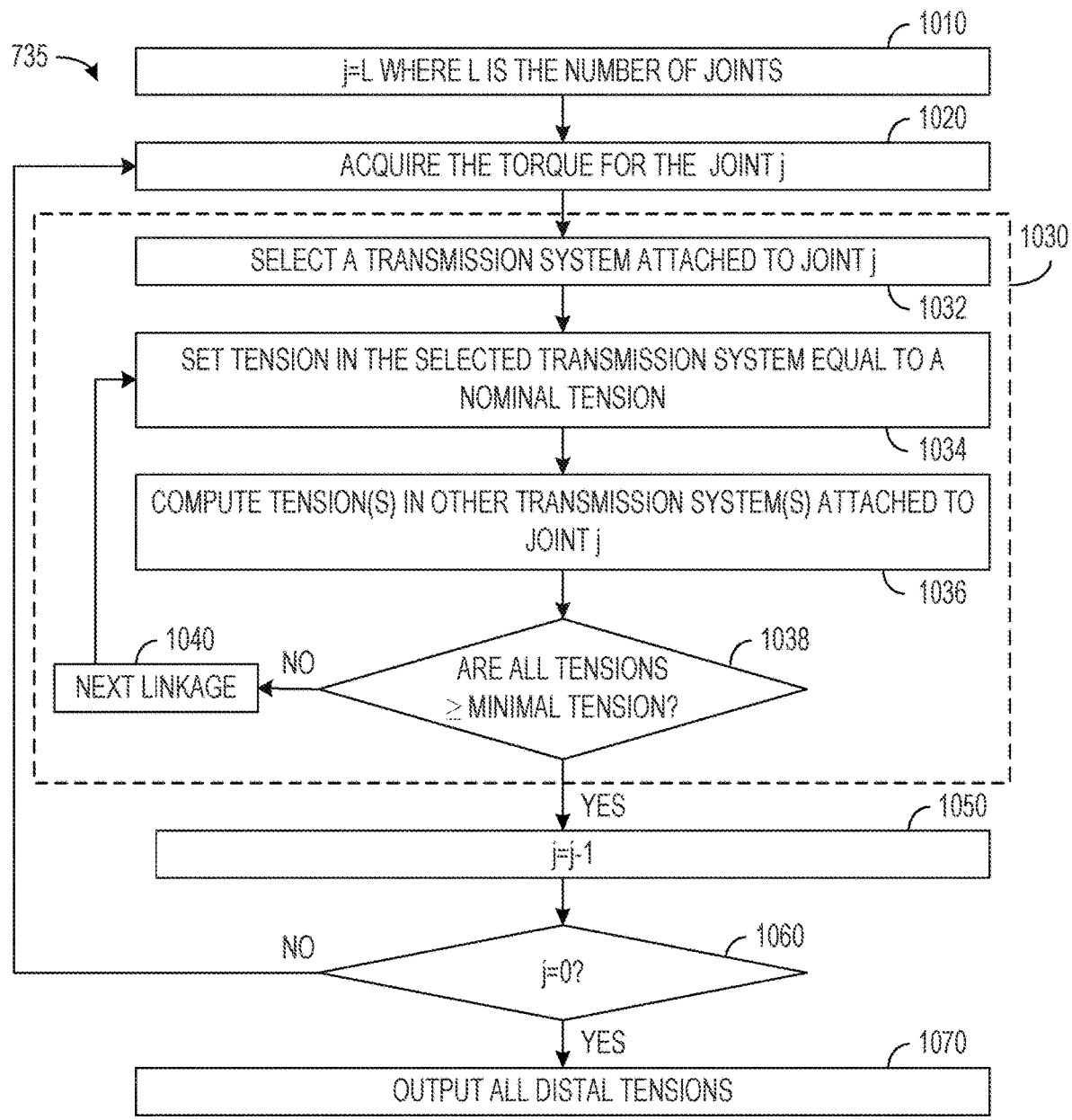
FIG. 11 is a flow diagram illustrating a process in accordance with an embodiment of the invention that determines tensions through sequential evaluation of joints in a multi jointed instrument.

An example process 1100 in which offset tensions are dynamically varied is described herein with respect to FIG. 11. In addition, further examples of enforcing a nominal tension other than a minimum tension $T_{MIN}$ for a transmission system is described with respect to process 1100 of FIG. 11 herein. In these examples, bias parameter $\tau_{BIAS}$ can be used to enforce the nominal tension.

Rather than being dynamically controlled, bias parameter $\tau_{BIAS}$ may be statically controlled during a portion of the surgical procedure or during an entire surgical procedure so that bias parameter $\tau_{BIAS}$ is maintained at a particular desired value even if tensions in one or more of transmission systems 620 decreases to values below minimum tension $T_{MIN}$. For example, bias parameter $\tau_{BIAS}$ can be statically controlled to avoid large tensions in transmission systems 620 that can increase a likelihood of damaging transmission systems 620.

A statically controlled bias parameter $\tau_{BIAS}$ provides constant offset tensions that are independent of current tensions of transmission systems 620, and are also independent of current positions of joints 610. The resulting offset tensions can offset tensions of the transmission systems 620 by different amounts or by the same amount. For example, in some cases, two or more of the constant offset tensions are equal to one another. In some cases, two or more of the constant offset tensions are different from one another. Some of the constant offset tensions may be equal to another, while some of the constant offset tensions may differ from one another.

In such examples, rather than dynamically varying bias parameter $\tau_{BIAS}$ such that bias parameter $\tau_{BIAS}$ varies at each measurement interval, bias parameter $\tau_{BIAS}$ is selected for a particular measurement interval and the selected bias parameter $\tau_{BIAS}$ is applied for one or more subsequent measurement intervals. In the one or more subsequent measurement intervals, bias parameter $\tau_{BIAS}$ remains set at the initial value selected at the particular measurement interval. The offset tensions provided by the selected bias parameter $\tau_{BIAS}$ thus remain the same during the one or more subsequent measurement intervals even if one or more of current tensions $T_1$ to $T_M$ falls below minimum tension $T_{MIN}$. While current tensions $T_1$ to $T_M$ may be increased or decreased in response to achieve the desired configuration for joints 610, the constraint to enforce minimum tension $T_{MIN}$ only causes changes to tensions $T_1$ to $T_M$ during the particular measurement interval, not during the one or more subsequent measurement intervals.

Alternatively, bias parameter $\tau_{BIAS}$ is selected and maintained for an entire surgical procedure. In some examples, bias parameter $\tau_{BIAS}$ is selected based on a number of uses of instrument 600. If instrument 600 is a multi-use instrument, each use of instrument 600 can alter characteristics of transmission systems 620. For example, if instrument 600 includes springs or other mechanical devices to provide offset tensions to transmission systems 620, these mechanical devices can relax over multiple uses of instrument 600. The software-enforced offset tensions provided by bias parameter $\tau_{BIAS}$ can increase after each use in response to relaxation of the hardware-enforced offset tensions.

In some examples, bias parameter $\tau_{BIAS}$ is selected based on a torque range for instrument 600 during a medical operation, or a range of motion for joints 610 during the medical operation. For example, for smaller torque ranges or smaller ranges of motion, e.g., less than 50%, less than 40%, or less than 30% of the entire ranges of motions for joints 610, bias parameter $\tau_{BIAS}$ can be selected to provide greater constant offset tensions such that smaller manipulations of joints 610 can be more easily achieved. In particular, greater constant offset tensions can increase responsiveness of transmission systems 620 and hence allow for torque provided by actuators 640 to more easily transfer to joints 610.

In some implementations, rather than being controlled statically or dynamically for an entirety of a surgical procedure, bias parameter $\tau_{BIAS}$ can be controlled in a hybrid manner in which bias parameter $\tau_{BIAS}$ is statically controlled for a portion of the surgical procedure and dynamically controlled for another portion of the surgical procedure. For example, bias parameter $\tau_{BIAS}$ can be controlled dynamically in accordance to the process described herein with respect to Equation 5A when tensions $T_1$ to $T_M$ are each less than or equal to a predefined threshold tension. Bias parameter $\tau_{BIAS}$ can be controlled statically when one or more of tensions $T_1$ to $T_M$ are greater than or equal to the predefined threshold tension. For example, the bias parameter $\tau_{BIAS}$ is maintained at a constant predefined value when one or more of tensions $T_1$ to $T_M$ are greater than or equal to the threshold tension. In such cases, bias parameter $\tau_{BIAS}$ is variable when tensions in transmission systems 620 are each less than or equal to the threshold tension, bias parameter $\tau_{BIAS}$ is fixed when tension in one or more of transmission systems 620 is greater than or equal to the threshold tension. In particular, bias parameter $\tau_{BIAS}$ is varied depending on the tensions in transmission systems 620 when bias parameter $\tau_{BIAS}$ is variable, and is fixed at a predefined value regardless of values of tensions in transmission systems 620 when bias parameter $\tau_{BIAS}$ is fixed. In this hybrid approach, at lower tensions, the dynamic control of bias parameter $\tau_{BIAS}$ can inhibit one or more of transmission systems 620 from becoming slack. At higher tensions, the static control of bias parameter $\tau_{BIAS}$ can reduce the likelihood that tensions $T_1$ to $T_M$ increase to levels that can damage the transmission systems 620.

Alternatively, when controlled in the hybrid manner, bias parameter $\tau_{BIAS}$ can be controlled dynamically in accordance to the process described herein with respect to Equation 5A when tensions $T_1$ to $T_M$ are each greater than or equal to a predefined threshold tension. As described herein, bias parameter $\tau_{BIAS}$ can be used to enforce a nominal tension other than a minimum tension $T_{MIN}$. For example, the nominal tension could be a maximum tension $T_{MAX}$. Bias parameter $\tau_{BIAS}$ can be controlled statically when one or more of tensions $T_1$ to $T_M$ are less than or equal to the predefined threshold tension. For example, the bias parameter $\tau_{BIAS}$ is maintained at a constant predefined value when one or more of tensions $T_1$ to $T_M$ are less than or equal to the threshold tension. In such cases, bias parameter $\tau_{BIAS}$ is variable when tensions in transmission systems 620 are each greater than or equal to the threshold tension, bias parameter $\tau_{BIAS}$ is fixed when tension in one or more of transmission systems 620 is less than or equal to the threshold tension. In this hybrid approach, at higher tensions, the dynamic control of bias parameter $\tau_{BIAS}$ can inhibit one or more of transmission systems 620 from exceeding a certain maximum tension $T_{MAX}$. At lower tensions, the static control of bias parameter $\tau_{BIAS}$ can increase the stiffnesses of transmission systems by applying constant offset tensions.

In some implementations, a parameter for enforcing minimum torque $\tau_{MIN}$, minimum tension $T_{MIN}$, or other nominal tension is monitored for error detection. For example, the parameter can correspond to bias constant $\tau_{BIAS}$ or tension degree of freedom $\theta_T$. In examples in which tension degree of freedom $\theta_T$ is monitored for error detection, variation in tension degree of freedom $\theta_T$ can be indicative of one or more faults associated with one or more of transmission systems 620. For instance, because this parameter is dependent on positions of actuators 640 but is independent of positions of joints 610, positions of actuators 640 can vary without a corresponding change in positions of joints 610 if transmission systems 620 are faulty and not transferring force from actuators 640 to joints 610. Accordingly, tension degree of freedom $\theta_T$ being greater than or equal to a predefined threshold value can be indicative of a fault associated with transmission systems 620. For example, the fault may correspond to one or more of transmission systems 620 including a broken tendon or other faulty force transfer member. When transmission systems 620 experience faults, tension degree of freedom $\theta_T$ can increase to a value greater than or equal to the predefined threshold value. For example, in cases in which encoders are used to determine positions of joints 610, positions of joints 610 are not directly measured and positions of actuators 640 are used to determine positions of joints 610. As a result, when transmission systems 620 experience faults, actuators 640 are repositioned to drive transmission systems 620 even though this repositioning of the actuators 640 does not cause repositioning of joints 610. Actuators 640 are thus repositioned to drive transmission system 620 without causing a corresponding change in positions of joints 610 that would be expected if transmission systems 620 were functioning properly. Actuators 640 continue to be driven to attempt to achieve the desired configuration, and because the desired configuration cannot be achieved, actuators 640 are driven such that tension degree of freedom $\theta_T$ continues to increase.

In response to tension degree of freedom $\theta_T$ being greater than or equal to the predefined threshold value, control system 650 controls a user output device, e.g., a speaker, a display, a vibration device, or other device that can provide audible, visual, or tactile feedback, to generate an alert to provide feedback to the operator. In addition, control system 650 can cease driving of actuators 640 until the fault of transmission systems 620 is addressed.

In some implementations, rather than issuing the alert in response to a value tension degree of freedom $\theta_T$ being greater than or equal to the predefined threshold value, the control system 650 issues the alert in response to a rate of change of tension degree of freedom $\theta_T$ being greater than or equal to the predefined threshold value. The rate of change can increase rapidly when transmission systems 620 are broken because transmission systems 620, when broken, do not provide resistance that actuators 640 would otherwise have to drive against in order to reposition joints 610. Furthermore, because joints 610 cannot achieve the desired configuration when actuators 640 are driven, control system 650 can continue to drive actuators 640, thereby causing the value of and the rate of change of tension degree of freedom θ_T to increase. Monitoring these values and providing alerts when they are greater than or equal to predefined values can ensure that faults associated with transmission systems 620 can be detected.

While the process associated with Equation 5A controls bias torques based on positions of actuators 640 and positions of joints 610, in some implementations, actuator torques $\tau_{A1}$ to $\tau_{AM}$ and transmission system tensions $T_1$ to $T_M$ are selected based on a damping function. One or more of the current velocities of actuators 640 is determined. Based on the one or more current velocities, a damping function is determined. The damping function is defined by one or more parameters such as a damping coefficient, a natural frequency, or other appropriate parameters that can be used to provide a dampening effect on movement of actuators 640 and joints 610. The damping function is selected to inhibit sudden changes in positions of actuators 640 and accordingly inhibit sudden changes in movement of joints 610. The damping function can be introduced to reduce tensions when actuators 640 are operated at high velocities. For example, in situations when actuators 640 are driven in one direction and then quickly driven in a different direction or are driven such that stiffnesses of transmission systems 620 are quickly reduced, the quick change in actuator motion can cause cables or tendons of transmission systems 620 to go slack. This can cause the cables or tendons to unwind from actuators 640. The damping function can be introduced to prevent this from occurring.

Figure 8A:
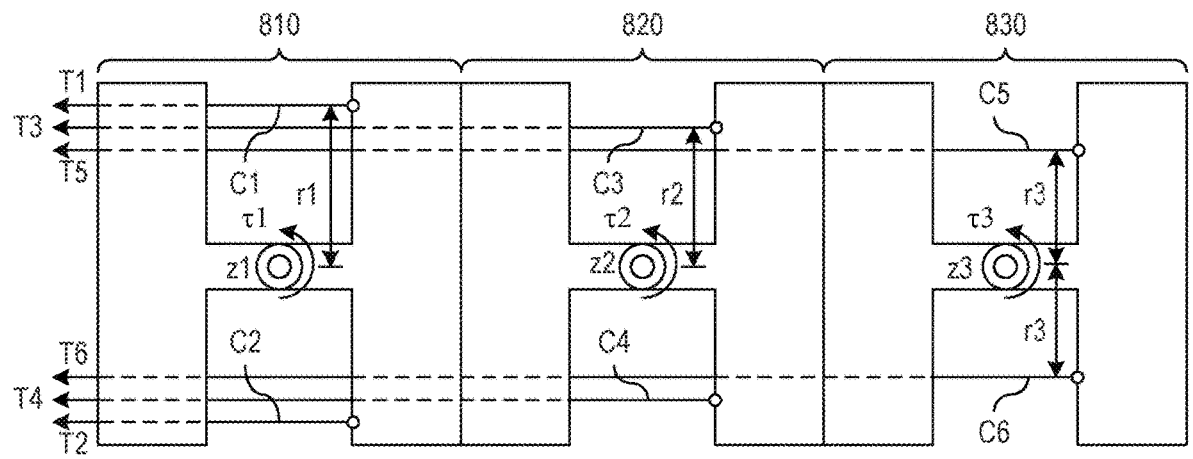
FIG. 8A is a side view of a portion of a multi jointed instrument that can be operated using drive force control in accordance of an embodiment of the invention to control joints with parallel actuation axes.

FIG. 8A, for example, illustrates a portion of an instrument that includes multiple mechanical joints 810, 820, and 830. Each joint 810, 820, or 830 provides a single degree of freedom, which corresponds to rotation about an axis z1, z2, or z3 of the joint. In FIG. 8A, tendons C1 and C2 connect to joint 810 for actuation of joint 810. Tendons C3 and C4 pass through joint 810 and connect to joint 820 for actuation of joint 820. Tendons C5 and C6 pass through joints 810 and 820 and connect to joint 830 for actuation of joint 830. The proximal ends (not shown) of tendons C1 to C6 can be connected though compliant transmission systems such as illustrated in FIG. 2 or 3A to respective drive motors or other actuators. The control system for the instrument controls the actuators to apply respective tensions T1, T2, T3, T4, T5, and T6 in tendons C1, C2, C3, C4, C5, and C6.

Joint 830 is at the distal end of the instrument in the illustrated embodiment, and actuation of joint 830 could be controlled using a single-joint process such as described above with reference to FIGS. 5A, 5B, 5C, and 5D. However, the total torque on joint 820 depends not only on the tensions in cables C3 and C4 but also the torque applied by tendons C5 and C6, which are connected to joint 830. The total torque on joint 810 similarly depends not only on the tensions in tendons C1 and C2 but also the torque applied by tendons C3, C4, C5, and C6, which are connected to joints 820 and 830 that are closer to the distal end. Models based on the geometric or kinematic characteristics of the instrument can be developed to relate the torques τ1, τ2, and τ3 on joints 810, 820, and 830 to the tension in tendons T1, T2, T3, T4, T5, and T6. Equation 4A illustrates one such mathematical model and provides a specific example of Equation 4 above. In Equation 4A, $\tau_1$, $\tau_2$, and $\tau_3$ are the respective actuating torques on joints 810, 820, and 830, $r_1$, $r_2$, and $r_3$ are the effective moment arms at which tendons C1, C3, and C5 attach, and T1, T2, T3, T4, T5, and T6 are the tensions in respective tendons C1, C2, C3, C4, C5, and C6. The model that leads to Equation 4A applies to a specific set of geometric or mechanical characteristics of the instrument including joints 810, 820, and 830 including that: rotation axes z1, z2, and z3 are parallel and lie in the same plane; tendons C1 and C2, C3 and C4, or C5 and C6 respectively attach at effective moment arm r1, r2, or r3; and tendons C1, C3, and C5 operate on respective joints 810, 820, and 830 in rotation directions opposite from the operation of tendons C2, C4, and C6, respectively.

$$\begin{bmatrix} \tau_1 \\ \tau_2 \\ \tau_3 \end{bmatrix} = \begin{bmatrix} r_1 & -r_1 & r_2 & -r_2 & r_3 & -r_3 \\ 0 & 0 & r_2 & -r_2 & r_3 & -r_3 \\ 0 & 0 & 0 & 0 & r_3 & -r_3 \end{bmatrix} \cdot \begin{bmatrix} T1 \\ T2 \\ T3 \\ T4 \\ T5 \\ T6 \end{bmatrix} \qquad \text{Equation 4A}$$

Figure 8B:
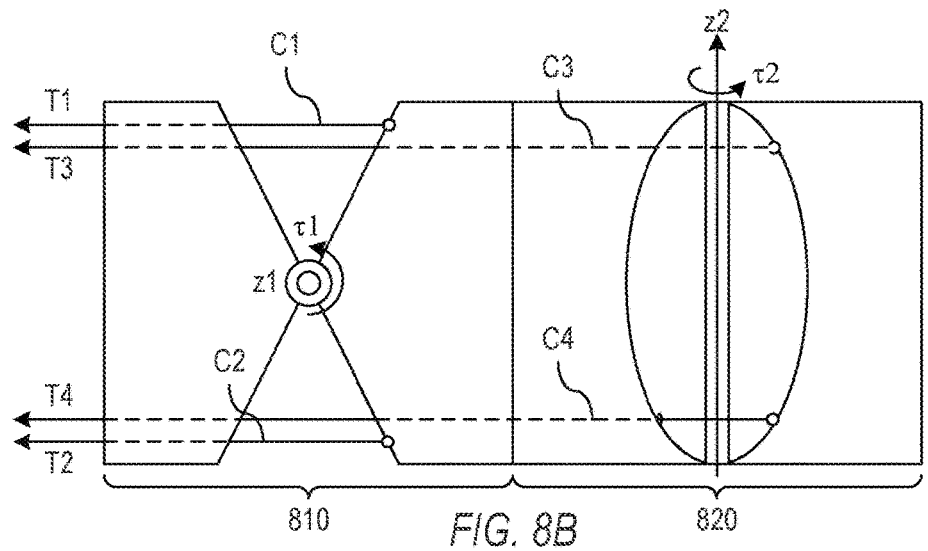
FIGS. 8B and 8C respectively show side and end views of a portion of a multi jointed instrument having joints with perpendicular actuation axes that can be operated using drive force control in accordance with an embodiment of the invention.
Figure 8C:
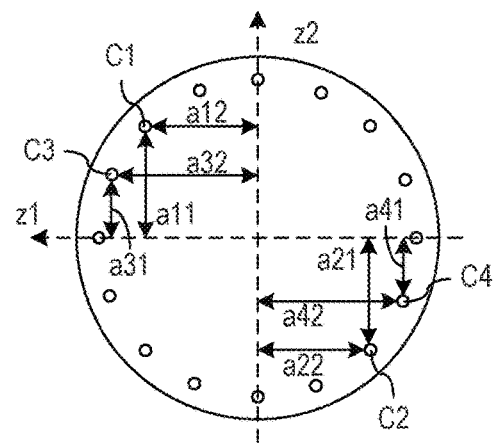

FIGS. 8B and 8C illustrate characteristics of a medical instrument including joints 810 and 820 with respective rotation axes z1 and z2 that are perpendicular to each other. In general, the net torque at each joint 810 and 820 depends on the tensions in the tendons passing through the joint to the distal end and the effective moment arms associated with the tendons relative to the actuation axis of the joint. FIG. 8C shows a view of a base of joint 810 to illustrate a typical example in which each tendon C1, C2, C3, and C4 operates at different moment arms about axes z1 and z2. Considering joints 810 and 820 as an isolated system or the last two actuated joints on the distal end of an instrument, the net torques $\tau_1$ and $\tau_2$ on joints 810 and 820 are related to the tensions T1, T2, T3, and T4 in respective tendons C1, C2, C3, and C4 as indicated in Equation 4B. In particular, joint 820 is subject to a net torque T2 that depends on tension T3 in tendon C3 and a moment arm α32 relative to axis z2 at which tendon C3 attaches to joint 820 and the tension T4 in tendon C4 and a moment arm α42 relative to axis z2 at which tendon C4 attaches to joint 820. Torque $\tau_1$ on joint 810 depends on the tensions T1 and T2 in the tendons C1 and C2 attached to joint 810, the tensions T3 and T4 in the tendons C3 and C4 attached to joint 820, and the moment arms α11, α21, α31, and α41. Moment arms α21 and α41 are assigned with a negative sign because pulling tendons C2 and C4 creates the rotation in a direction opposite from the convention-defined positive direction for torque $\tau_1$ on joint 810. For the same reason, moment arm α31 is also assigned with a negative sign as pulling tendon C3 causes rotation opposite to the direction of positive rotation of joint 820.

$$\begin{bmatrix} \tau_1 \\ \tau_2 \end{bmatrix} = \begin{bmatrix} a11 & -a21 & a31 & -a41 \\ 0 & 0 & -a32 & a42 \end{bmatrix} \begin{bmatrix} T1 \\ T2 \\ T3 \\ T4 \end{bmatrix} \qquad \text{Equation 4B}$$

It should be appreciated that a similar method to compute the matrix A in Equation 4 can be employed when the joint axes are neither parallel or perpendicular to each other but rather at an arbitrary relative orientation, by computing accordingly the moment arms of each tendon with respect to each joint axis.

Figure 9A:
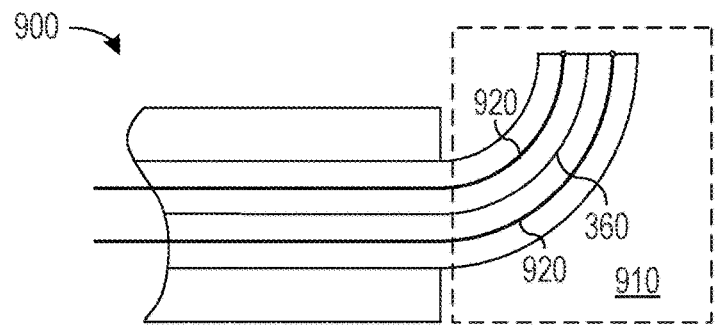
FIG. 9A shows an embodiment of the invention in which a joint includes a continuously flexible structure that provides two degrees of freedom of motion.
Figure 9B:
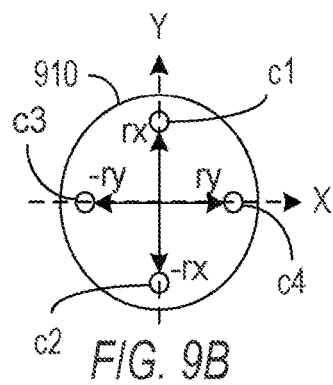
FIGS. 9B and 9C illustrate embodiments of the invention respectively employing four and three tendons to control two degrees of freedom of motion in the joint of FIG. 9A.

FIG. 9A shows a portion 900 of an instrument including a continuous flexible joint 910 such as is commonly found in medical catheters, endoscopes for the gastrointestinal tract, the colon and the bronchia, guide wires, and some other endoscopic instruments such as graspers and needles used for tissue sampling. Joint 910 is similar to the flexible structure described above with reference to FIG. 3B. However, joint 910 is manipulated through the use of three or more tendons 920 to provide a joint with two degrees of freedom of motion. For example, FIG. 9B shows a base view of an embodiment in which four tendons 920, which are labeled c1, c2, c3, and c4 in FIG. 9B, connect to an end of flexible joint 910. A difference in the tensions in tendons c1 and c2 can turn joint 910 in a first direction, e.g., cause rotation about an X axis, and a difference in the tensions in tendons c3 and c4 can turn joint 910 in a second direction that is orthogonal to the first direction, e.g., cause rotation about a Y axis. The components $\tau_X$ and $\tau_Y$ of the net torque tending to bend joint 910 can be determined from tensions T1, T2, T3, and T4 respectively in tendons c1, c2, c3, and c4 as indicated in Equation 4C. As can be seen from Equation 4C, equations for torque components $\tau_X$ and $\tau_Y$ are not coupled in that component $\tau_X$ depends only on tensions T1 and T2 and component $\tau_Y$ depends only on tensions T3 and T4.

$$\begin{bmatrix} \tau_X \\ \tau_Y \end{bmatrix} = \begin{bmatrix} rx & -rx & 0 & 0 \\ 0 & 0 & ry & -ry \end{bmatrix} \begin{bmatrix} T1 \\ T2 \\ T3 \\ T4 \end{bmatrix} \quad \text{Equation 4C}$$

Figure 9C:
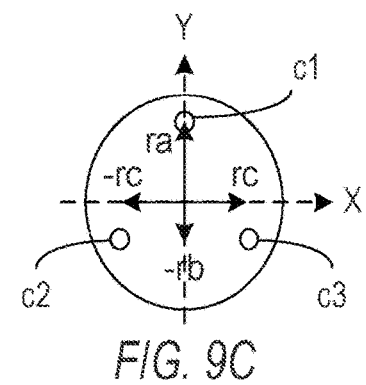

FIG. 9C illustrates a base view of an embodiment that uses three tendons 920, which are labeled c1, c2, and c3 in FIG. 9C, to actuate joint 910. With this configuration, the components $\tau_X$ and $\tau_Y$ of the net torque tending to bend joint 910 can be determined from tensions T1, T2, and T3 respectively in tendons c1, c2, and c3 as indicated in Equation 4D where ra is the moment arm of tendon c1 about the X axis, -rb is the moment arm of tendons c2 and c3 about the X axis, and rc and -rc are the respective moment arms of tendons c2 and c3 about the Y axis. Moment arms of tendons c2 and c3 about X-axis are assigned with a negative sign by convention because pulling tendons c2 and c3 will bend joint 910 in a direction opposite from the direction that pulling tendon c1 bends joint 910 about the X axis. For the same reason, the moment arm of tendon c3 about Y-axis is assigned a negative sign by convention.

$$\begin{bmatrix} \tau_X \\ \tau_Y \end{bmatrix} = \begin{bmatrix} ra & -rb & -rb \\ 0 & rc & -rc \end{bmatrix} \begin{bmatrix} T1 \\ T2 \\ T3 \end{bmatrix} \quad \text{Equation 4D}$$

Figure 9D:
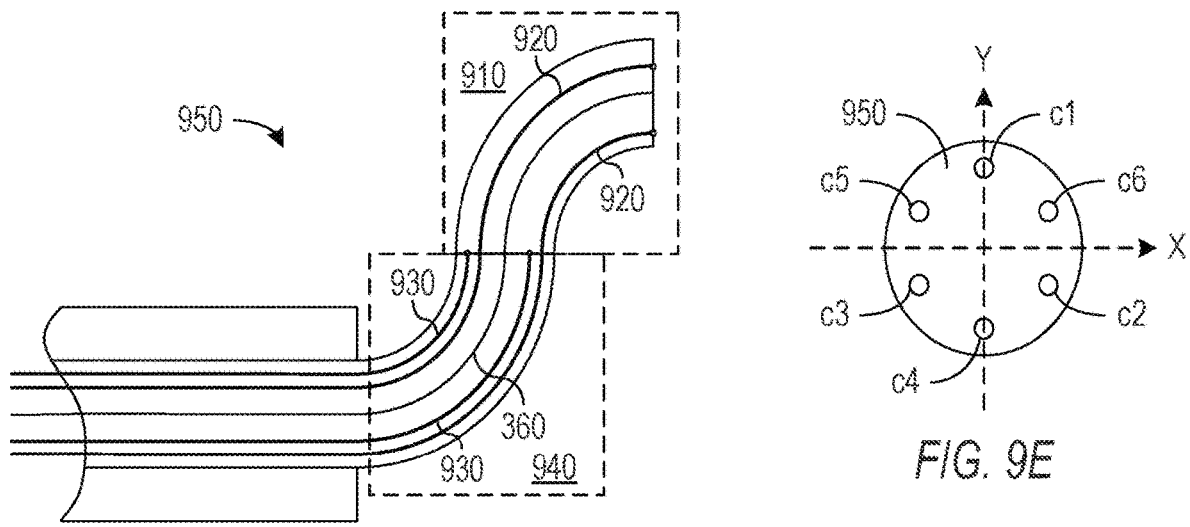
FIG. 9D shows an embodiment of a two jointed medical instrument in which each joint includes a continuously flexible structure and provides two degrees of freedom of motion.
Figure 9E:
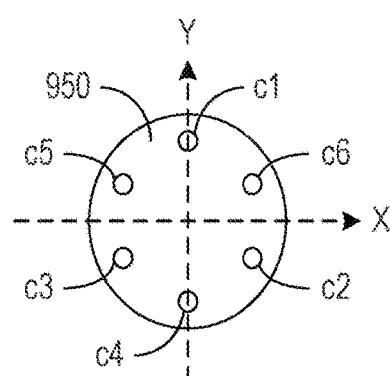
FIG. 9E illustrates an embodiment of the invention employing six tendons to control four degrees of freedom of motion provided by the two joints in the instrument of FIG. 9D.

FIG. 9D illustrates an embodiment in which a flexible instrument 950, e.g., a flexible catheter, contains two joints. A joint 910 is actuated through tendons 920 to provide two degrees of freedom of motion, and a joint 940 is actuated through tendons 930 to provide another two degrees of freedom of motion. FIG. 9E illustrates the base of joint 940 in a specific case that uses three tendons 920 (labeled c1, c2, and c3 in FIG. 9E) for joint 910 and three tendons 930 (labeled c4, c5, and c6 in FIG. 9E) for joint 940. The relationships between torques and forces in the most distal joint 910 may be modeled using Equation 4D above. However, the torques in joint 940 depend on the tensions in all of the tendons 920 and 930 that pass through joint 940. In this example, the joint 940 is implemented using a flexible section. The torques and tensions in instrument 950 may thus be related in one specific example as indicated in Equation 4E. In Equation 4E, $\tau 1_X$ and $\tau 1_Y$ are torque components in joint 910, $\tau 2_X$ and $\tau 2_Y$ are torque components in joint 940, ra, rb, and rc are the magnitudes of moment arms, T1, T2, and T3 are tensions in tendons 920, and T4, T5, and T6 are tensions in tendons 930.

$$\begin{bmatrix} \tau 2_X \\ \tau 2_Y \\ \tau 1_X \\ \tau 1_Y \end{bmatrix} = \begin{bmatrix} -ra & rb & rb & ra & -rb & -rb \\ 0 & -rc & rc & 0 & rc & -rc \\ 0 & 0 & 0 & ra & -rb & -rb \\ 0 & 0 & 0 & 0 & rc & -rc \end{bmatrix} \begin{bmatrix} T1 \\ T2 \\ T3 \\ T4 \\ T5 \\ T6 \end{bmatrix} \quad \text{Equation 4E}$$

Equations 4A to 4E illustrate that in many medical instruments the problem of finding tensions that provide a particular torque in the most distal joint can be solved independently of the other tensions in the system. More generally, the joint torque for each joint depends on the tensions in the tendons that connect to that joint and on the tensions applied to more distal joints. Step 735 of processes 700 and 700B of FIGS. 7A and 7B can thus be performed using a process that iteratively analyzes joints in a sequence from the distal end of the instrument toward the proximal end of the instrument to determine a set of tensions that produces a given set of joint torques.

Figure 10:
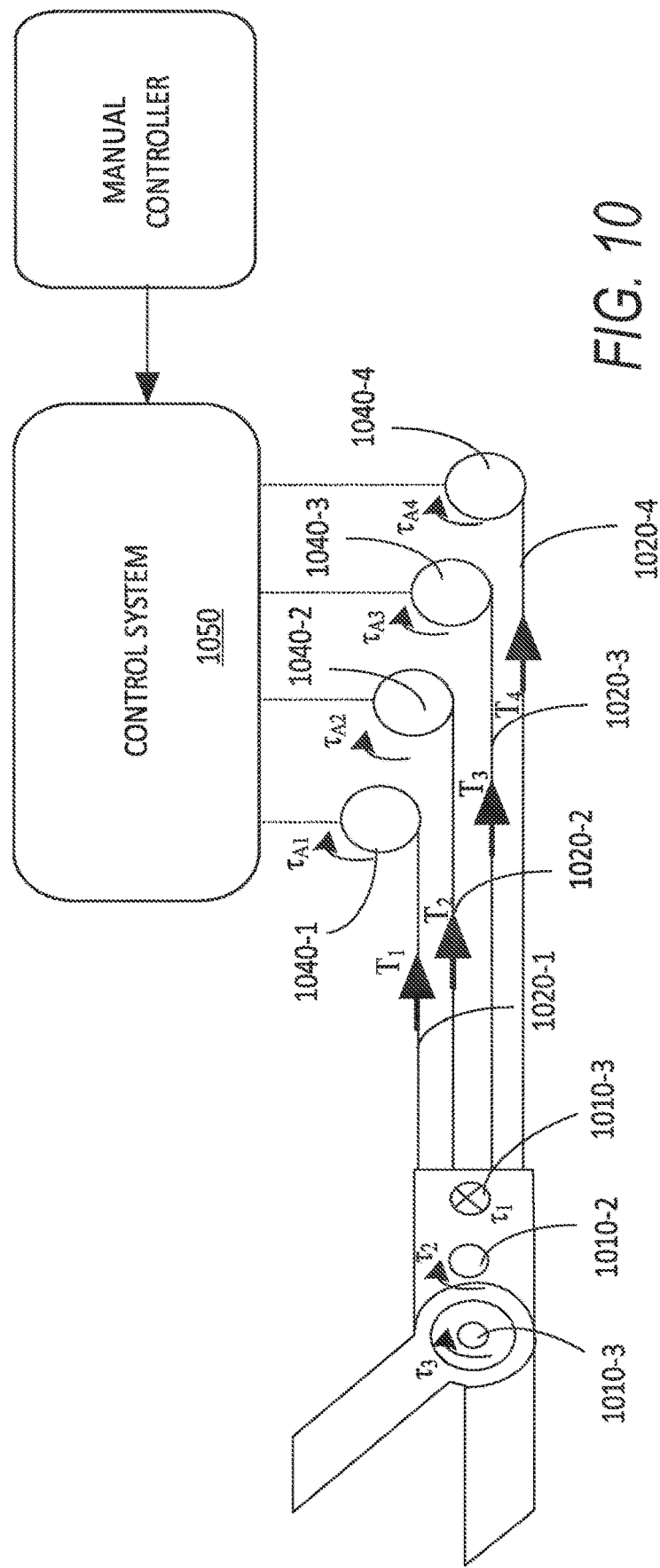
FIG. 10 schematically illustrates a robotic medical system and particularly shows quantities used in another embodiment of the invention that controls a multi jointed instrument.

FIG. 10 illustrates an embodiment in which an instrument 1000 includes three joints 1010-1, 1010-2, 1010-3, generically referred to as joints 1010. Each joint 1010 is actuated through four tendons 1020-1, 1020-2, 1020-3, 1020-4, generically referred to as tendons 1020, to provide a degree of freedom of motion. Actuators 1040-1, 1040-2, 1040-3, 1040-4, generically referred to as actuators 1040, are coupled to tendons 1020 so that torques $\tau_{A1}$ and $\tau_{A4}$ applied to actuators 1040 are transmitted distally through tendons 1020 to joints 1010. Torques $\tau_{A1}$ to $\tau_{A4}$ generate tensions $T_1$ to $T_4$ in tendons 1020. Each joint 1010 is coupled to each of tendons 1020 such that a position of each joint 1010 is adjusted when any one tendon 1020 is actuated by a corresponding actuator 1040. Torques $\tau_1$ to $\tau_3$ can correspond to a pitch torque, a yaw torque, and a grip torque. The pitch torque is depicted in FIG. 10 as generating motion perpendicular to a plane of motion for the yaw torque. Torques $\tau_1$ to $\tau_3$ are applied to joints 1010 when actuators 1040 apply torques $\tau_{A1}$ to $\tau_{A4}$.

The control system 1050 can operate actuators 1040 to generate tensions in tendons 1020. The control system 1050 can enforce a minimum tension $T_{MIN}$ such that tension in each of tendons 1020 exceeds a selected minimum tension $T_{MIN}$. As a result, the relationships between actuator positions and degrees of freedom can be derived using Equation 2A, with the number of actuators M being equal to 4 and the number of degrees of freedom of motion N being equal to 3. In this regard, relationships between actuator positions $\theta_{A1}$ to $\theta_{A4}$ and degrees of freedom $\theta_1$ to $\theta_3$ and $\theta_T$ may be modeled using Equation 2B below ($\theta = C\theta_A$). In this embodiment, $\theta_1$ to $\theta_3$ correspond to degrees of freedom of motion, e.g., a pitch degree of freedom, a yaw degree of freedom, and a grip degree of freedom. $\theta_T$ corresponds to a tension degree of freedom to be used for constraining tensions in tendons 1020 to be greater than or equal to a minimum tension $T_{MIN}$. The coefficients $b_{IJ}$ for index I=1 to 4 and index J=1 to 4 are selected such that the column associated with the tension degree of freedom $\theta_T$ is linearly independent of the other degrees of freedom. The coefficients $b_{IJ}$ by further represent the coupling between actuator positions and joint positions.

$$\begin{bmatrix} \theta_1 \\ \theta_2 \\ \theta_3 \\ \theta_T \end{bmatrix} = \begin{bmatrix} b_{11} & b_{12} & b_{13} & b_{14} \\ b_{21} & b_{22} & b_{23} & b_{24} \\ b_{31} & b_{32} & b_{33} & b_{34} \\ b_{41} & b_{42} & b_{43} & b_{44} \end{bmatrix} \begin{bmatrix} \theta_{A1} \\ \theta_{A2} \\ \theta_{A3} \\ \theta_{A4} \end{bmatrix} \quad \text{Equation 2B}$$

Equation 5A can be used to derive the relationships between actuator torques and joint torques. In particular, the relationships between actuator torques $\tau_{A1}$ and $\tau_{A4}$ and joint torques $\tau_1$ to $\tau_3$ and $\tau_{BIAS}$ may be modeled using Equation 5B below ($\tau_A = D[\tau_1, \tau_2, \tau_3, 0]^T + D[0, 0, 0, \tau_{BIAS}]$). Matrix D of Equation 5B can be determined by taking the transpose of coupling Matrix C of Equation 2B. Bias parameter $\tau_{BIAS}$ can be determined using the processes described with respect to Equation 5A. Equation 5B can be used to determine the actuator torques to apply to actuators 1040.

$$\begin{bmatrix} \tau_{A1} \\ \tau_{A2} \\ \tau_{A3} \\ \tau_{A4} \end{bmatrix} = \begin{bmatrix} d_1 & d_{12} & d_{13} & d_{14} \\ d_{21} & d_{22} & d_{23} & d_{24} \\ d_{31} & d_{32} & d_{33} & d_{34} \\ d_{41} & d_{42} & d_{43} & d_{44} \end{bmatrix} \begin{bmatrix} \tau_1 \\ \tau_2 \\ \tau_3 \\ 0 \end{bmatrix} + \begin{bmatrix} d_{11} & d_{12} & d_{13} & d_{14} \\ d_{21} & d_{22} & d_{23} & d_{24} \\ d_{31} & d_{32} & d_{33} & d_{34} \\ d_{41} & d_{42} & d_{43} & d_{44} \end{bmatrix} \begin{bmatrix} 0 \\ 0 \\ 0 \\ \tau_{BIAS} \end{bmatrix} \quad \text{Equation 5B}$$

Referring to FIG. 11, process 1100 is an iterative process used for computing tensions that produce a given set of joint torques. Process 1100 can use a process similar to that described for Equation 5A to offset the torques applied by the actuators and thereby offset the tensions applied to the transmission systems. In particular, $\tau_{BIAS}$ can be selected to provide offset tensions that achieve a particular nominal or target tension.

In the example shown in FIG. 11, process 1100 starts with a tension determination for the last or most distal joint and then sequentially determines tensions for joints in an order toward the first or most proximal joint. Step 1110 initializes an index j, which identifies a joint for analysis and is initially set to the number L of joints. Step 1120 then acquires the torque $\tau_j$ for the jth joint. The joint torque $\tau_j$ may, for example, be determined as in step 730 of process 700 or step 732 of 700B as described above and may have a single non-zero component for a joint providing a single degree of freedom of motion or two non-zero components for a joint providing two degrees of freedom of motion.

Step 1130 then calculates the tensions to be directly applied to the jth joint through the linkages attached to the jth joint in order to produce the net torque, e.g., computed in step 730 or 732 of FIG. 7A or 7B. In the example of FIG. 11, computation of step 1130 is under the constraint that one of the directly applied tensions is a target or nominal tension. The nominal tension may be but is not required to be zero so that tension in the transmission system is released or alternatively the minimum tension $T_{MIN}$ that ensures that the tendons in the transmission systems do not become slack. The nominal tension may but is not required to correspond to a case in which actuator force is released, e.g., where actuators 640 of FIG. 6 are freewheeling, in which case the tension may depend on type of transmission system employed.

In the specific case in which jth joint in the medical instrument provides a single degree of freedom of motion and is directly coupled to two tendons or transmission systems, the joint torque has a single component that is related to the tensions by a single equation from among Equation 4. Step 1130 for the Lth or most distal joint then involves solving a linear equation relating the joint torque to the two tensions coupled to the most distal joint. With a single linear equation involving two unknown tensions, applying the constraint that one tension is the nominal tension guarantees a unique solution for the other tension. In particular, the other tension can be uniquely determined from the torque on the most distal joint and the relevant coefficients of the coupling matrix A. Alternatively, if the Lth joint provides two degrees of freedom of motion and is coupled to three tendons or transmission systems, the joint torque has two components and corresponds to two equations from among the system of equations represented in Equation 4. The two equations involve three tensions, so that with the constraint that one of the tensions be equal to the nominal tension, the other two tensions can be uniquely determined from the components of the joint torque and the relevant components of the coupling matrix A. It should be noted that the proposed method is general in the sense that, in a similar fashion, if m tendons, with m greater than three, are connected to the same joint that provides two degrees of freedom, then (m−2) tensions can be constrained at the same time to be equal to the nominal tension, while the remaining two tensions will be uniquely determined from the components of the joint torque and the relevant components of the coupling matrix A.

Step 1130 is initially executed for the most distal joint (i.e., j=L). Substep 1132 of step 1130 initially selects one of the transmission systems attached to the most distal joint, and substep 1134 sets that tension to the minimum permitted tension $T_{MIN}$ for a trial calculation in substep 1136. Substep 1136 initially calculates tension (or tensions) for the other transmission systems attached to the joint, and the calculated tensions only depend on the computed joint torque and the other tensions directly applied to the most distal joint. Substep 1138 determines whether all of the calculated tensions are greater than or equal to the minimum permitted tension $T_{MIN}$. If not, step 1140 selects another of the transmission systems directly coupled to the joint to be the transmission system with the nominal tension when substeps 1134 and 1136 are repeated. Once step 1140 determines that the calculated tension or tensions are all greater than or equal to the minimum allowed tension $T_{MIN}$, the determination of the tension for the most distal joint is complete, and step 1150 decrements the joint index j before process 1100 branches back from step 1160 for repetition of step 1120.

Step 1130 for the jth joint in the case of a joint connected to two transmission systems and providing one degree of freedom of motion involves evaluation of a single equation from among the system of equations represented in Equation 5A. As described above, the nature of the coupling matrix A is such that the equation for the jth joint involves only the tensions directly coupled to the jth joint and the tensions coupled to more distal joints. Accordingly, if the tensions for more distal joints have already been determined, the equation associated with the jth joint involves only two unknowns, which are the tensions in the transmission systems directly connected to the joint. The constraint that one of the tensions be the nominal tension allows unique determination of the other tension that is larger than or equal to the nominal tension. The case where the jth joint connects to three transmission systems and provides two degrees of freedom of motion involves evaluation of the two equations associated with the two components of the joint torque. If the tensions for more distal joints have already been determined, the equations associated with the jth joint involves only three unknowns, which are the tensions in the tendons directly connected to the joint. The constraint that one of the tensions be the nominal tension allows unique determination of the other two tensions that are larger than or equal to the nominal tension.

Process 1100 of FIG. 11 can thus use tension determinations in the order of the joints from the distal end of the instrument to generate a complete set of distal tensions that is output in step 1170 when step 1160 determines that the most proximal joint has been evaluated. Process 1100 can be efficiently implemented using a computer or other computing system operating for real time determination of tensions that are changed at a rate that provides motion smooth enough for medical procedures, e.g., at rates of up to 250 Hz or more. Further, the constraint that each joint has at least one directly applied tension at a target or nominal value provides continuity between the tensions determined at successive times.

While substep 1134 is described as setting the tension in a selected transmission system to the minimum tension $T_{MIN}$ and substep 1138 is described as determining whether all of the tensions are above the minimum tension $T_{MIN}$, in other implementations, the nominal tension for substep 1134 differs from the threshold tension of substep 1138. The nominal tension can be a target tension for at least one of the transmission systems, and the threshold tension can be a tension that the calculated tensions in the transmission systems do not exceed or do not fall below. In this regard, the threshold tension can be greater than or equal to the nominal tension if the threshold tension is a maximum tension $T_{MAX}$, or can be less than or equal to the nominal tension if the threshold tension is a minimum tension $T_{MIN}$.

While step 1130 is described with respect to achieving tensions above a (non-zero) minimum tension $T_{MIN}$, in some implementations, the nominal tension is a maximum allowed tension $T_{MAX}$ or some other tension in between the minimum tension $T_{MIN}$ and the maximum tension $T_{MAX}$. Rather than determining whether all of the calculated tensions are greater than or equal to the minimum permitted tension $T_{MIN}$, substep 1138 determines whether all of the calculated tensions are less than or equal to the maximum allowed tension $T_{MAX}$. In other implementations, when the nominal tension is between the maximum allowed tension $T_{MAX}$ and the minimum allowed tension $T_{MIN}$, either all of the calculated tensions are greater than or equal to the nominal tension or all of the calculated tensions are less than or equal to the nominal tension.

In some implementations, Process 1100 is executed in conjunction with one or more steps of Process 500. For example, any of the corrections described herein, such as but not limited to those provided by steps 530, 535, 540, 550, 740, and 745, can be applied to Process 1100. These corrections may override the tensions computed as part of step 1130. In this regard, the calculated tensions at steps 1130, 1150, 1160 can be overridden such that the applied distal tensions may differ from the calculated tensions. For example, if the nominal tension is a minimum tension $T_{MIN}$ or some other nominal tension below which the calculated tensions do not fall, the calculated tensions may saturate at a maximum tension $T_{MAX}$ to prevent the transmission systems from being damaged from excessive tensions. If the nominal tension is a maximum tension $T_{MAX}$ or some other nominal tension above which the calculated tensions do not exceed, the calculated tensions may saturate at a minimum tension $T_{MIN}$ to prevent the transmission systems from going slack. The processes described above and elsewhere in this disclosure can be implemented or controlled using software that may be stored on computer readable media such as electronic memory or magnetic or optical disks for execution by a general purpose computer. Alternatively, control of or calculations employed in the above-described processes can be implanted using application-specific hardware or electronics.

Figure 12A:
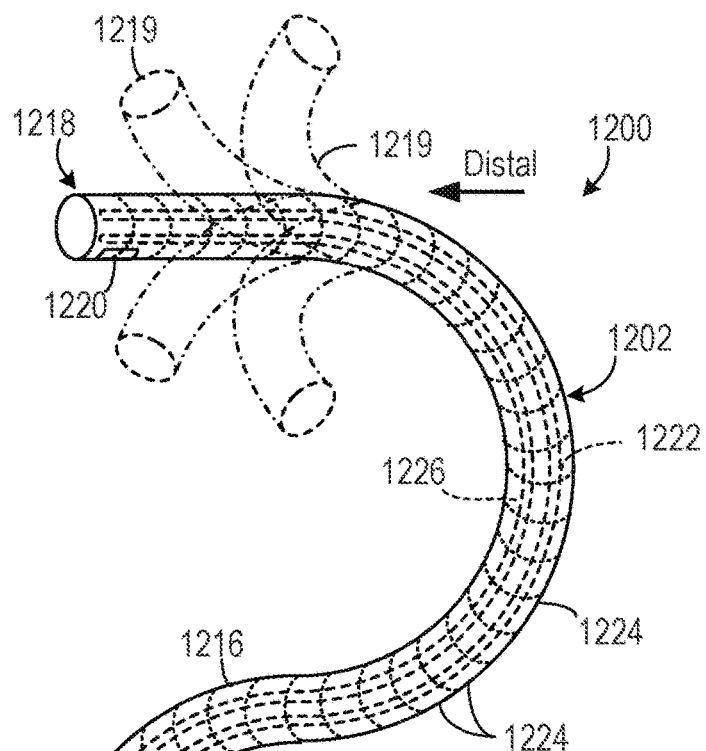
FIG. 12A is a simplified diagram of a medical instrument system according to some embodiments.

Although the invention has been described with reference to particular embodiments, the description is only an example of the invention's application and should not be taken as a limitation. For example, types of instruments that can be controlled vary in implementations. FIG. 12A is a simplified diagram of another example of a medical instrument system 1200 according to some embodiments. In some embodiments, medical instrument system 1200 may be used as medical instrument in an image-guided medical procedure performed with a teleoperated or non-teleoperated medical system. In some examples, medical instrument system 1200 may be used for non-teleoperational exploratory procedures or in procedures involving traditional manually operated medical instruments, such as endoscopy. Optionally medical instrument system 1200 may be used to gather (i.e., measure) a set of data points corresponding to locations within anatomic passageways of a patient, such as patient P.

Medical instrument system 1200 includes elongate device 1202 coupled to a drive unit 1204. Elongate device 1202 includes a flexible body 1216 having proximal end 1217 and distal end 1218 (also called "tip portion 1218" when the distal end includes a portion of a tip). In some embodiments, flexible body 1216 has an approximately 3 mm outer diameter. Other flexible body outer diameters may be larger or smaller.

Medical instrument system 1200 further includes a tracking system 1230 for determining the position, orientation, speed, velocity, pose, and/or shape of flexible body 1216 at distal end 1218 and/or of one or more segments 1224 along flexible body 1216 using one or more sensors and/or imaging devices as described in further detail below. The entire length of flexible body 1216, between distal end 1218 and proximal end 1217, may be effectively divided into segments 1224. Tracking system 1230 may optionally be implemented as hardware, firmware, software or a combination thereof which interact with or are otherwise executed by one or more computer processors, which may include the processors of control system 150 in FIG. 1.

Tracking system 1230 may optionally track distal end 1218 and/or one or more of the segments 1224 using a shape sensor 1222. Shape sensor 1222 may optionally include an optical fiber aligned with flexible body 1216 (e.g., provided within an interior channel (not shown) or mounted externally). In one embodiment, the optical fiber has a diameter of approximately 1200 μm. In other embodiments, the dimensions may be larger or smaller. The optical fiber of shape sensor 1222 forms a fiber optic bend sensor for determining the shape of flexible body 1216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 1216 may be determined using other techniques. For example, a history of the distal end pose of flexible body 1216 can be used to reconstruct the shape of flexible body 1216 over the interval of time. In some embodiments, tracking system 1230 may optionally and/or additionally track distal end 1218 using a position sensor system 1220. Position sensor system 1220 may be a component of an EM sensor system with position sensor system 1220 including one or more conductive coils that may be subjected to an externally generated electromagnetic field. Each coil of EM sensor system including the position sensor system 1220 then produces an induced electrical signal having characteristics that depend on the position and orientation of the coil relative to the externally generated electromagnetic field. In some embodiments, position sensor system 1220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 1230 may alternately and/or additionally rely on historical pose, position, or orientation data stored for a known point of an instrument system along a cycle of alternating motion, such as breathing. This stored data may be used to develop shape information about flexible body 1216. In some examples, a series of positional sensors (not shown), such as electromagnetic (EM) sensors similar to the sensors in position sensor system 1220 may be positioned along flexible body 1216 and then used for shape sensing. In some examples, a history of data from one or more of these sensors taken during a procedure may be used to represent the shape of elongate device 1202, particularly if an anatomic passageway is generally static.

Figure 12B:
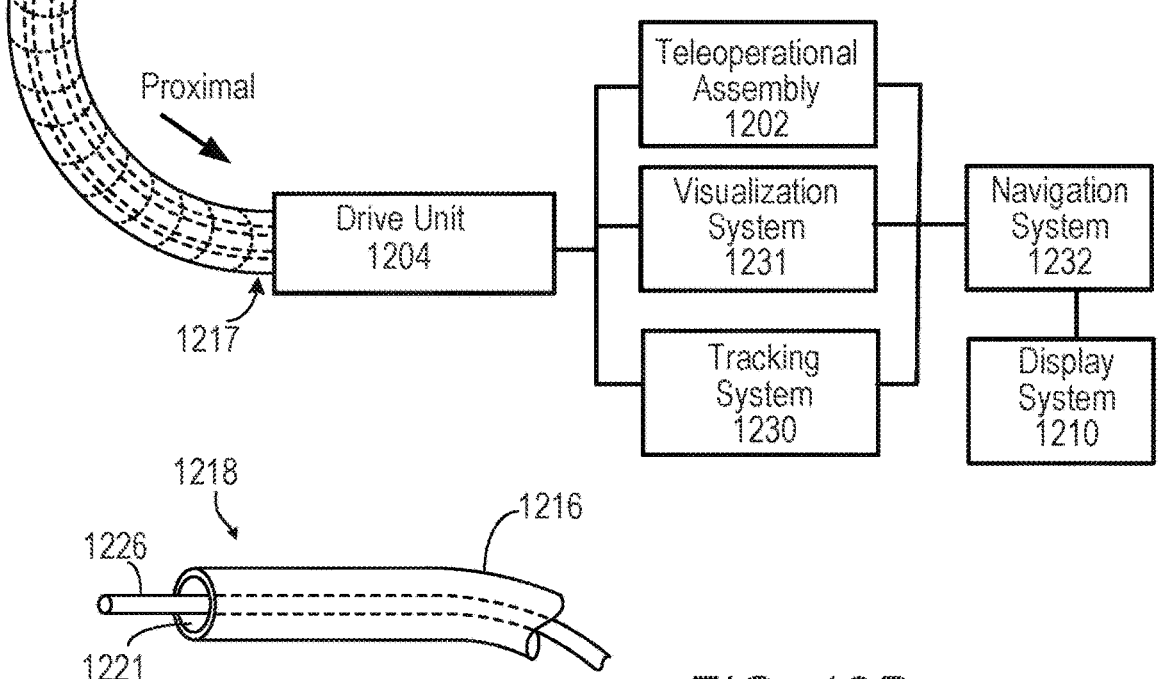
FIG. 12B is a simplified diagram of a medical instrument with an extended medical tool according to some embodiments.

Flexible body 1216 includes a channel 1221 sized and shaped to receive a medical instrument 1226. FIG. 12B is a simplified diagram of flexible body 1216 with medical instrument 1226 extended according to some embodiments. In some embodiments, medical instrument 1226 may be used for procedures such as surgery, biopsy, ablation, illumination, irrigation, or suction. Medical instrument 1226 can be deployed through channel 1221 of flexible body 1216 and used at a target location within the anatomy. Medical instrument 1226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 1226 is a biopsy instrument, which may be used to remove sample tissue or a sampling of cells from a target anatomic location. Medical instrument 1226 may be used with an image capture probe also within flexible body 1216. In various embodiments, medical instrument 1226 may be an image capture probe that includes a distal portion with a stereoscopic or monoscopic camera at or near distal end 1218 of flexible body 1216 for capturing images (including video images) that are processed by a visualization system 1231 for display and/or provided to tracking system 1230 to support tracking of distal end 1218 and/or one or more of the segments 1224. The image capture probe may include a cable coupled to the camera for transmitting the captured image data. In some examples, the image capture instrument may be a fiber-optic bundle, such as a fiberscope, that couples to visualization system 1231. The image capture instrument may be single or multi-spectral, for example capturing image data in one or more of the visible, infrared, and/or ultraviolet spectrums. Alternatively, medical instrument 1226 may itself be the image capture probe. Medical instrument 1226 may be advanced from the opening of channel 1221 to perform the procedure and then retracted back into the channel when the procedure is complete. Medical instrument 1226 may be removed from proximal end 1217 of flexible body 1216 or from another optional instrument port (not shown) along flexible body 1216.

Medical instrument 1226 may additionally house cables, linkages, or other actuation controls (not shown) that extend between its proximal and distal ends to controllably bend distal end of medical instrument 1226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 1216 may also house cables, linkages, or other steering controls (not shown) that extend between drive unit 1204 and distal end 1218 to controllably bend distal end 1218 as shown, for example, by broken dashed line depictions 1219 of distal end 1218. In some examples, at least four cables are used to provide independent "up-down" steering to control a pitch of distal end 1218 and "left-right" steering to control a yaw of distal end 1281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 1200 is actuated by a teleoperational assembly, drive unit 1204 may include drive inputs that removably couple to and receive power from drive elements, such as actuators, of the teleoperational assembly. In some embodiments, medical instrument system 1200 may include gripping features, manual actuators, or other components for manually controlling the motion of medical instrument system 1200. Elongate device 1202 may be steerable or, alternatively, the system may be non-steerable with no integrated mechanism for operator control of the bending of distal end 1218. In some examples, one or more lumens, through which medical instruments can be deployed and used at a target surgical location, are defined in the walls of flexible body 1216.

In some embodiments, medical instrument system 1200 may include a flexible bronchial instrument, such as a bronchoscope or bronchial catheter, for use in examination, diagnosis, biopsy, or treatment of a lung. Medical instrument system 1200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 1230 may be sent to a navigation system 1232 where it is combined with information from visualization system 1231 and/or the pre-operatively obtained models to provide the physician, clinician, or surgeon or other operator with real-time position information. In some examples, the real-time position information may be displayed on a display system 1210 for use in the control of medical instrument system 1200. In some examples, a control system may utilize the position information as feedback for positioning medical instrument system 1200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 1200 may be teleoperated. In some embodiments, teleoperational manipulator assembly 1233 may be replaced by direct operator control. In some examples, the direct operator control may include various handles and operator interfaces for hand-held operation of the instrument.

Various adaptations and combinations of features of the embodiments disclosed are within the scope of the invention as defined by the following claims.

What is claimed is:

1. A medical instrument system including:
   a plurality of actuators;
   a medical instrument comprising
      an end portion, and
      a plurality of transmission systems, each transmission system coupling the end portion to an actuator of the plurality of actuators such that the plurality of actuators is operable to drive the plurality of transmission systems to move the end portion; and
   a control system operably connected to the plurality of actuators, the control system configured to execute operations comprising:
      determining a difference between a current configuration of the end portion and a desired configuration of the end portion, and
      operating the plurality of actuators to apply a plurality of tensions to the plurality of transmission systems based on the difference and based on constant offset tensions, the constant offset tensions being independent of current tensions experienced by the plurality of transmission systems.

2. The instrument system of claim 1, wherein:
   the plurality of tensions, when applied to the plurality of transmission systems, generate a desired net torque at the end portion, and
   the constant offset tensions, when applied to the plurality of transmission systems, generate a zero net torque at the end portion.

3. The instrument system of claim 1, wherein at least two offset tensions of the constant offset tensions are equal.

4. The instrument system of claim 1, wherein at least two offset tensions of the constant offset tensions differ.

5. The instrument system of claim 1, wherein operating the plurality of actuators to apply the plurality of tensions comprises:
   operating the plurality of actuators such that an average of the plurality of tensions is maintained.

6. The instrument system of claim 1, wherein the operations further comprise determining the constant offset tensions based on a number of uses of the medical instrument, a torque range for the medical instrument during a medical operation, or a range of motion for the end portion during the medical operation.

7. The instrument system of claim 1, wherein:
   operating the plurality of actuators to apply the plurality of tensions comprises: when one or more of the current tensions is greater than or equal to a predefined tension, operating the plurality of actuators to apply the plurality of tensions, and
   the operations further comprise:
      when the one or more of the current tensions is less than the predefined tension, operating the plurality of actuators to apply a plurality of second tensions to the plurality of transmission systems based on the difference and based on a minimum tension, a second tension of the plurality of second tensions being no less than the minimum tension.

8. The instrument system of claim 7, wherein the second tension of the plurality of second tensions is equal to the minimum tension.

9. The instrument system of claim 7, wherein operating the plurality of actuators to apply the plurality of second tensions comprises operating the plurality of actuators to inhibit slack in all transmission systems of the transmission systems.

10. The instrument system of claim 7, wherein operating the plurality of actuators to apply the plurality of tensions comprises:
    determining baseline torques based on the desired configuration,
    adjusting the baseline torques such that the plurality of tensions of the transmission systems are each above the minimum tension, and
    applying the adjusted baseline torques to the plurality of actuators.

11. The instrument system of claim 10, wherein adjusting the baseline torques comprises:
    determining a biasing torque to adjust a baseline torque in one of the transmission systems such that tension in the one of the transmission systems is above the minimum tension, the biasing torque being a maximum of a plurality of biasing torques to adjust the baseline torques of the transmission systems such that the tensions in the transmission systems are each above the minimum tension, and
    adjusting each of the baseline torques based on the biasing torque.

12. The instrument system of claim 1, wherein operating the plurality of actuators to apply the plurality of tensions comprises:
    operating the plurality of actuators such that a tension of the plurality of tensions is maintained at a maximum tension and a remainder of the plurality of tensions is no more than the maximum tension.

13. The instrument system of claim 1, wherein the operations further comprise:
    determining a current velocity of an actuator of the plurality of actuators, and
    determining a damping function based on the current velocity and a desired velocity of the actuator of the plurality of actuators, wherein operating the plurality of actuators to apply the plurality of tensions comprises operating the plurality of actuators to apply the plurality of tensions based on the damping function.

14. The instrument system of claim 1, wherein the plurality of transmission systems is configured to be slack when the plurality of transmission systems is decoupled from the plurality of actuators.

15. The instrument system of claim 1, wherein each actuator of the plurality of actuators is coupled to a single transmission system of the plurality of transmission systems.

16. The instrument system of claim 1, wherein each actuator of the plurality of actuators is operable to move the end portion in multiple degrees of freedom of motion.

17. A method of operating an instrument, the method comprising:
    determining, by one or more computer processors, a difference between a current configuration and a desired configuration of an end portion of the instrument; and
    operating, by the one or more computer processors, a plurality of actuators to apply a plurality of tensions to a plurality of transmission systems, the transmission systems coupled to move the end portion, the tensions based on the difference and constant offset tensions, the constant offset tensions being independent of current tensions experienced by the plurality of transmission systems.

18. The method of claim 17, wherein
    the plurality of tensions, when applied to the plurality of transmission systems, generate a desired net torque at the end portion, and
    the constant offset tensions, when applied to the plurality of transmission systems, generate a zero net torque at the end portion.

19. The method of claim 17, wherein operating, by the one or more computer processors, the plurality of actuators to apply the plurality of tensions comprises:
    operating, by the one or more computer processors, the plurality of actuators such that an average of the plurality of tensions is maintained.

20. The method of claim 17, wherein:
    operating, by the one or more computer processors, the plurality of actuators to apply the plurality of tensions comprises: when one or more of the current tensions is greater than or equal to a predefined tension, operating, by the one or more computer processors, the plurality of actuators to apply the plurality of tensions, and
    the method further comprises:
        when the one or more of the current tensions is less than the predefined tension, operating the plurality of actuators to apply a plurality of second tensions to the plurality of transmission systems based on the difference and based on a minimum tension, a second tension of the plurality of second tensions being no less than the minimum tension.

21. The method of claim 17, wherein operating, by the one or more computer processors, the plurality of actuators to apply the plurality of tensions comprises:
    operating, by the one or more computer processors, the plurality of actuators such that a tension of the plurality of tensions is maintained at a maximum tension and a remainder of the plurality of tensions is no more than the maximum tension.

22. The method of claim 17, further comprising:
    determining, by the one or more computer processors, a current velocity of an actuator of the plurality of actuators, and
    determining, by the one or more computer processors, a damping function based on the current velocity and a desired velocity of the actuator of the plurality of actuators,
    wherein operating, by the one or more computer processors, the plurality of actuators to apply the plurality of tensions comprises operating, by the one or more computer processors, the plurality of actuators to apply the plurality of tensions based on the damping function.

23. A non-transitory computer readable medium storing instructions that are executable by a processing device, and upon such execution cause the processing device to perform a method of operating an instrument, the method comprising:
    determining a difference between a current configuration and a desired configuration of an end portion of the instrument; and
    operating a plurality of actuators to apply a plurality of tensions to a plurality of transmission systems, the transmission systems coupled to move the end portion, the tensions based on the difference and constant offset tensions, the constant offset tensions being independent of current tensions experienced by the plurality of transmission systems.

24. The computer readable medium of claim 23, wherein operating the plurality of actuators to apply the plurality of tensions comprises:
    operating the plurality of actuators such that an average of the plurality of tensions is maintained.

25. The computer readable medium of claim 23, wherein:
    operating the plurality of actuators to apply the plurality of tensions comprises: when one or more of the current tensions is greater than or equal to a predefined tension, operating the plurality of actuators to apply the plurality of tensions, and
    the method further comprises:
        when the one or more of the current tensions is less than the predefined tension, operating the plurality of actuators to apply a plurality of second tensions to the plurality of transmission systems based on the difference and based on a minimum tension, a second tension of the plurality of second tensions being no less than the minimum tension.

26. The computer readable medium of claim 23, wherein operating the plurality of actuators to apply the plurality of tensions comprises:
    operating the plurality of actuators such that a tension of the plurality of tensions is maintained at a maximum tension and a remainder of the plurality of tensions is no more than the maximum tension.

* * * * *